US010531847B2

(12) United States Patent
Jang et al.

(10) Patent No.: US 10,531,847 B2
(45) Date of Patent: Jan. 14, 2020

(54) X-RAY DETECTOR AND X-RAY IMAGING APPARATUS HAVING THE SAME

(71) Applicant: Samsung Electronics Co., Ltd., Suwon-si (KR)

(72) Inventors: Kyoung Choul Jang, Suwon-si (KR); Dae Soo Kim, Yongin-si (KR); Seong Hwa Park, Suwon-si (KR); Jin-Ho Choi, Anyang-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 226 days.

(21) Appl. No.: 15/653,165

(22) Filed: Jul. 18, 2017

(65) Prior Publication Data

US 2018/0014800 A1    Jan. 18, 2018

(30) Foreign Application Priority Data

Jul. 18, 2016 (KR) .................. 10-2016-0090577
Jan. 17, 2017 (KR) .................. 10-2017-0008009

(51) Int. Cl.
*A61B 6/00*    (2006.01)

(52) U.S. Cl.
CPC .............. *A61B 6/44* (2013.01); *A61B 6/4441* (2013.01); *A61B 6/566* (2013.01); *A61B 6/4405* (2013.01); *A61B 6/484* (2013.01)

(58) Field of Classification Search
CPC ....... A61B 6/44; A61B 6/4405; A61B 6/4441; A61B 6/484; A61B 6/566
See application file for complete search history.

(56) References Cited

U.S. PATENT DOCUMENTS

| | | | |
|---|---|---|---|
| 2005/0056789 A1 | 3/2005 | Spahn et al. | |
| 2009/0065703 A1 | 3/2009 | Jadrich et al. | |
| 2010/0054404 A1* | 3/2010 | Watanabe | A61B 6/00 378/62 |
| 2010/0124698 A1* | 5/2010 | Wu | H01M 2/1066 429/100 |
| 2011/0272588 A1 | 11/2011 | Jadrich et al. | |
| 2012/0069966 A1* | 3/2012 | Kobayashi | A61B 6/00 378/189 |
| 2016/0081649 A1* | 3/2016 | Enomoto | A61B 6/56 378/189 |
| 2016/0154119 A1* | 6/2016 | Kim | G03B 42/025 378/204 |

* cited by examiner

*Primary Examiner* — David P Porta
*Assistant Examiner* — Fani P Boosalis

(57) ABSTRACT

Disclosed is an X-ray detector having impact resistance and an X-ray imaging apparatus having the X-ray detector. The X-ray imaging apparatus comprises an X-ray source for generating and irradiating X-rays and an X-ray detector for detecting the X-rays irradiated from the X-ray source. The X-ray detector comprises a main body having a bottom plate including a joining groove, a detector panel arranged inside the main body for converting X-rays irradiated from the X-ray source into electric signals, and a middle block arranged inside the main body to support the detector panel. The middle block has a boss configured to protrude toward the bottom plate of the main body. The boss is inserted into the joining groove. A buffer member is arranged in at least part of the joining groove to prevent the boss from coming into contact with the joining groove.

19 Claims, 21 Drawing Sheets

X-RAY DETECTOR AND X-RAY IMAGING APPARATUS HAVING THE SAME

CROSS-REFERENCE TO RELATED APPLICATIONS

The present application is related to and claims benefit of Korean Patent Application No. 10-2016-0090577, filed Jul. 18, 2016 and Korean Patent Application No. 10-2017-0008009, filed Jan. 17, 2017, the disclosures of which are incorporated herein by reference in their entireties.

TECHNICAL FIELD

The present disclosure relates to an X-ray detector and an X-ray imaging apparatus having the same, and more particularly, to an X-ray detector having impact resistance and an X-ray imaging apparatus having the X-ray detector.

BACKGROUND

X-ray imaging apparatuses are devices that use x-ray radiation to obtain images of the inside of an object. The X-ray imaging apparatus irradiates an object with X-rays and images the inside of the object in a non-invasive manner by detecting the X-rays that have penetrated the object. Accordingly, a medical X-ray imaging apparatus may be used to diagnose internal injuries or diseases, which may not be noticeable from the appearance of the object.

The X-ray imaging apparatus may include an X-ray source for generating and irradiating an object with X-rays and an X-ray detector for detecting X-rays that have penetrated the object. The X-ray source may be movably arranged so as to image different parts of the object. The X-ray detector may be used in a table mode in which X-ray detector is mounted on a scan table, a stand mode in which the X-ray detector is mounted on a scan stand, or a portable mode in which the X-ray detector is not fixed in one position.

An external shock applied to the X-ray detector may tend to degrade the performance of the X-ray detector. Specifically, if an external shock is directly applied to a vulnerable part, such as a detector panel, a circuit board, etc., it is likely to damage or break the vulnerable part, which causes degradation of performance of the X-ray detector.

SUMMARY

To address the above-discussed deficiencies, it is a primary object to provide an X-ray detector with an improved structure to prevent a detector panel from being damaged from an external shock and an X-ray imaging apparatus including the X-ray detector.

The present disclosure also provides an X-ray detector with an improved structure to protect a detector panel from appearance deformation of the X-ray detector, and an X-ray imaging apparatus including the X-ray detector.

In accordance with one aspect of the present disclosure, an X-ray imaging apparatus comprises an X-ray source for generating and irradiating X-rays and an X-ray detector for detecting the X-rays irradiated from the X-ray source. The X-ray detector comprises a main body having a bottom plate in which a joining groove is formed, a detector panel arranged inside the main body for converting X-rays irradiated from the X-ray source into electric signals, a middle block arranged inside the main body to support the detector panel, and having a boss formed to protrude toward the bottom plate of the main body to be inserted into the joining groove and a buffer member arranged in at least part of the joining groove to prevent the boss from coming into contact with the joining groove.

The bottom plate includes an uplift part bent to the inside of the X-ray detector so as to form a battery receptacle on the outer side of the bottom plate and forms a wall of the joining groove. The buffer member includes a first buffer member arranged along the girth of the uplift part.

The bottom plate further includes a rib extending to the inside of the X-ray detector to be located outside of the uplift part and forms another wall of the joining groove. The buffer member further includes a second buffer member arranged along the girth of the rib.

The middle block is supported on the uplift part.

The buffer member has the form of a closed loop.

The detector panel is arranged inside the main body to be spaced apart from the main body.

The main body further comprises a side wall extending from the bottom plate in the width direction of the X-ray detector. The middle block is arranged inside the main body to be spaced apart from the side wall.

The X-ray detector further comprises a battery cover detachably combined onto the bottom plate of the main body to open/close the battery receptacle.

In accordance with one aspect of the present disclosure, an X-ray detector for detecting X-rays comprises a main body including a bottom plate in which a joining groove is formed, and a side wall extending from the bottom plate in the width direction of the X-ray detector, a detector panel arranged inside the main body spaced apart from the main body for converting the X-rays into electric signals, a middle block arranged inside the main body to support the detector panel, arranged to be spaced apart from a side wall of the main body, and having a boss formed to protrude toward the bottom plate of the main body to be inserted into the joining groove, a shock transfer path formed across the side wall and the bottom plate of the main body and a buffer member arranged in the shock transfer path to prevent an external shock from being delivered to the detector panel.

The buffer member is arranged in the joining groove.

The buffer member has the form of a closed loop.

The bottom plate includes an uplift part bent to the inside of the X-ray detector so as to form a battery receptacle on the outer side of the bottom plate and forms a wall of the joining groove. The buffer member is arranged along the girth of the uplift part to face the boss.

The bottom plate comprises a rib extending to the inside of the X-ray detector to be in parallel with the side wall spaced apart from the side wall of the main body, and forms a wall of the joining groove. The buffer member is arranged tightly against the rib.

The buffer member is arranged tightly against the rib to face the boss.

In accordance with one aspect of the present disclosure, an X-ray imaging apparatus comprises an X-ray source for generating and irradiating X-rays and an X-ray detector for detecting the X-rays irradiated from the X-ray source. The X-ray detector comprises a main body having a bottom plate in which a joining groove is formed, a detector panel arranged inside the main body for converting X-rays irradiated from the X-ray source into electric signals, a middle block arranged inside the main body to support the detector panel, and having a boss formed to protrude toward the bottom plate of the main body to be inserted into the joining groove and a fixing member combined onto the bottom plate in the opposite direction to a direction in which the boss is inserted into the joining groove so as to prevent movement of the middle block, thereby fixing the middle block onto the bottom plate.

The fixing member passes through the bottom plate and is combined with the boss of the middle block.

The detector panel is arranged inside the main body to be spaced apart from the main body.

The main body further comprises a side wall extending from the bottom plate in the width direction of the X-ray detector. The middle block is arranged inside the main body to be spaced apart from the side wall.

The bottom plate includes an uplift part bent to the inside of the X-ray detector so as to form a battery receptacle on the outer side of the bottom plate and forms a wall of the joining groove. The boss is inserted into the joining groove to be spaced apart from the uplift part.

The bottom plate further includes a rib extending to the inside of the X-ray detector to be located outside of the uplift part and forms another wall of the joining groove. The boss is inserted into the joining groove to be spaced apart from the uplift part.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 19, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Figure 1:
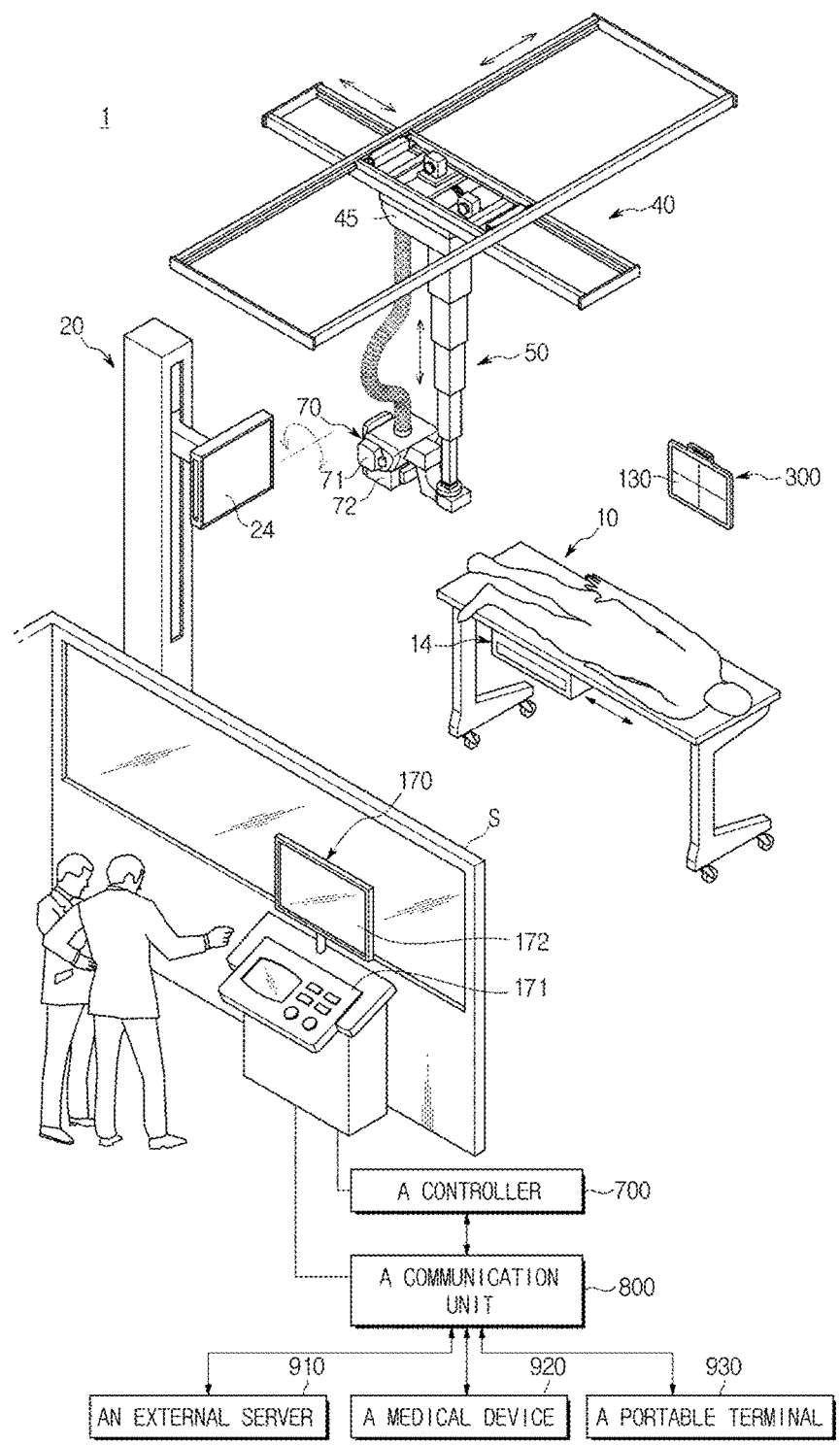
FIG. 1 illustrates a perspective view of an X-ray imaging apparatus, according to an embodiment of the present disclosure.
Figure 2:
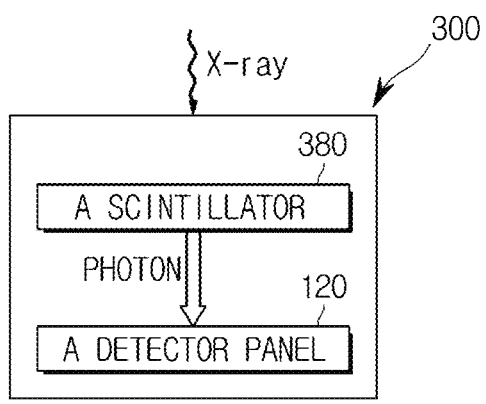
FIG. 2 illustrates a block diagram for explaining how a detector panel works in an X-ray imaging apparatus, according to an embodiment of the present disclosure.

Referring to FIGS. 1 to 2, a first embodiment where an X-ray detector 300 is applied will now be described.

FIG. 1 illustrates a perspective view of an X-ray imaging apparatus according to an embodiment of the present disclosure and FIG. 2 illustrates a block diagram for explaining how a detector panel works in an X-ray imaging apparatus according to an embodiment of the present disclosure.

As shown in FIG. 1, an X-ray imaging apparatus 1 may include an X-ray source 70 for generating and irradiating X-rays, the X-ray detector 300 for detecting X-rays that irradiate to and penetrate an object from the X-ray source 70, and a workstation 170 for receiving commands from a user and providing information. The X-ray imaging apparatus 1 may further include a scan table 10 and a scan stand 20 that may have the X-ray detector 300 equipped thereon. Furthermore, the X-ray imaging apparatus 1 may further include a controller 700 for controlling the X-ray imaging apparatus 1 according to input commands, and a communication unit 800 for communicating with an external device.

The X-ray source 70 is a device for irradiating an object with X-rays. The object (or subject) as used herein may be, but not exclusively, a living body of a human or animal, or anything whose internal structure may be imaged by the X-ray imaging apparatus 1.

The X-ray source 70 may include an X-ray tube 71 for generating X-rays and a collimator 72 for guiding the X-rays toward an object.

A guide rail 40 may be installed on the ceiling of an examination room where the X-ray imaging apparatus 1 is placed. The X-ray source 70 may be moved to a position corresponding to the object by being linked to a moving carriage 45 that moves along the guide rail 40. The moving carriage 45 and the X-ray source 70 may be linked through a foldable post frame 50 to adjust the altitude of the X-ray source 70.

The workstation 170 may be placed in an extra independent space S where X-rays are blocked, and connected to the X-ray source 70 and the X-ray detector 300 through wired or wireless communication.

The workstation 170 may be equipped with an input unit 171 for receiving commands from the user and a display 172 for displaying information.

The input unit 171 may receive commands to control a scan protocol, scan conditions, scan timing, positioning of the X-ray source 70, etc. The input unit 171 may include a keyboard, a mouse, a touch screen, a voice recognizer, etc.

The display 172 may display screens representing an image for guiding the input of the user, an X-ray image, and/or a state of the X-ray imaging apparatus 1.

The controller 700 may control scan timing, scan conditions, etc., of the X-ray source 70 at a command input from the user, and create a medical image with image data received from the X-ray detector 300. The controller 700 may also control e.g., positions of mounting units 14, 24 in which the X-ray source 70 or the X-ray detector 300 is equipped, according to the scan protocol and the position of the object.

The X-ray imaging apparatus 1 may be connected to an external device (e.g., an external server 910, a medical device 920, and a portable terminal 930, such as a smart phone, a tablet Personal Computer (PC), a wearable device, etc.) through the communication unit 800 for exchanging data.

In an embodiment, the X-ray detector 300 may be implemented as a fixed type X-ray detector fixed on the scan table 10. In another embodiment, it may be detachably equipped on the mounting units 14, 24. In yet another embodiment, the X-ray detector 300 may be implemented as a portable X-ray detector available at any place. The portable X-ray detector may further be classified into a wired type and a wireless type depending on data transfer methods or power supplying methods.

On one side of the X-ray source 70, there may be a sub user interface for providing information for the user and receiving commands from the user. Some or all of the functions performed by the input unit 171 and display 172 of the workstation 170 may be performed by the sub user interface.

While FIG. 1 illustrates a fixed type X-ray imaging apparatus attached onto the ceiling of an examination room, the X-ray imaging apparatus may include any of different types of X-ray imaging apparatus, such as a C-arm type of X-ray imaging apparatus, a mobile X-ray imaging apparatus, etc., within the scope of the present disclosure obvious to those of ordinary skill in the art.

The X-ray detector 300 is a device for detecting X-rays that have penetrated an object. An incident face 130 onto which X-rays are incident may be formed on the front face of the X-ray detector 300, and a detector panel 120 (see FIG. 2) may be arranged inside the X-ray detector 300.

The X-ray source 70 may generate X-rays and irradiate them to an object, and include an X-ray tube 71 for X-ray generation.

The X-ray detector 300 is a device for detecting X-rays that have been irradiated from the X-ray source 70 and have penetrated the object, and this X-ray detection is performed by the detector panel 120 inside the X-ray detector 300. Furthermore, the detector panel 120 converts the detected X-rays into electric signals, to obtain an image of the inside of the object.

The detector panel 120 may be classified based on a material composition method, a method for converting the detected X-rays to an electric signal, or a method for obtaining an electric signal.

First, the detector panel 120 may be divided into ones formed of a single element and ones formed of composite elements, based on the material composition method.

In the case the detector panel 120 is formed of a single material, a section that detects the X-rays and generates an electric signal and a section that reads and processes the electric signal may be formed of a semiconductor of a single material or may be manufactured with a single process, for example, using only a Charge Coupled Device (CCD) or only a Complementary Metal Oxide Semiconductor (CMOS).

In the case the detector panel 120 is formed of composite elements, a section that detects the X-rays and generates an electric signal and a section that reads and processes the electric signal may be formed of different materials or manufactured with different processes. For example, there may be an occasion where photo detectors, such as e.g., photo diodes, CCD, CdZnTe, etc., are used to detect X-rays, and CMOS Read Out Integrated Circuits (ROICs) are used to read and process the electric signal; an occasion where strip detectors are used to detect X-rays and the CMOS ROICs are used to read and process the electric signal; an occasion where a-Si or a-Se flat panel systems are used, and so on.

Furthermore, the detector panel 120 may be divided into having a direct conversion scheme and an indirect conversion scheme based on the method for converting the X-rays to an electric signal.

In the direct conversion scheme, when X-rays are irradiated, electron and hole pairs are generated temporarily inside the photo detector and electric potential across both electrodes of the photo detector causes the electrons to be moved to the positive electrode and the holes to be moved to the negative electrode. The detector panel 120 converts the movements into an electric signal. In the direct conversion scheme, the material used for the photo detector may be e.g., a-Se, CdZnTe, HgI2, PbI2, etc.

In the indirect conversion scheme, the X-rays irradiated from the X-ray source 70 (see FIG. 1) reacts with a scintillator 180 to cause photons having a visible wavelength in a visible spectrum to be emitted, and the photo detector detects the photons and converts them to an electric signal, as shown in FIG. 2. The material used for the photo detector in the indirect conversion scheme may be e.g., a-Si, and the scintillator 180 may be a GADOX scintillator in the form of a thin film, or a micro column type or needle structure type CSI (T1). In FIG. 2, the detector panel 120 is used as a photo detector.

Furthermore, the detector panel 120 may be divided into operating in a charge integration mode for storing charges for a certain period of time and obtaining a signal from the charges and operating in a photon counting mode for counting the occasion when a signal is generated by a single X-ray photon, based on the method for obtaining the electric signal.

The detector panel 120 may operate in any of the aforementioned modes.

Figure 3:
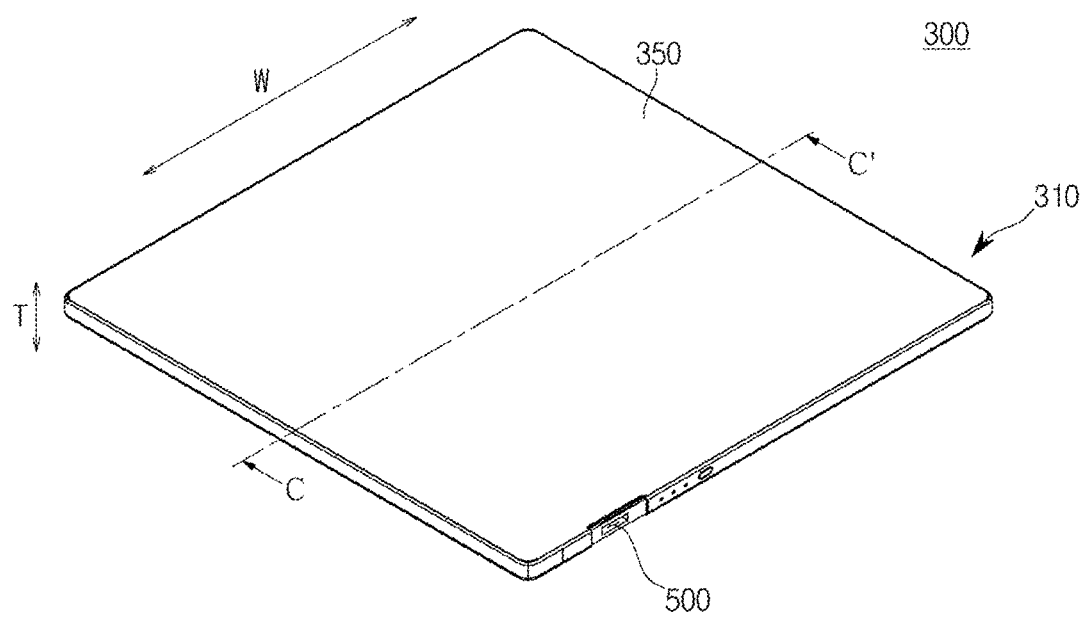
FIG. 3 illustrates a perspective view of an X-ray detector, according to a first embodiment of the present disclosure.
Figure 4:
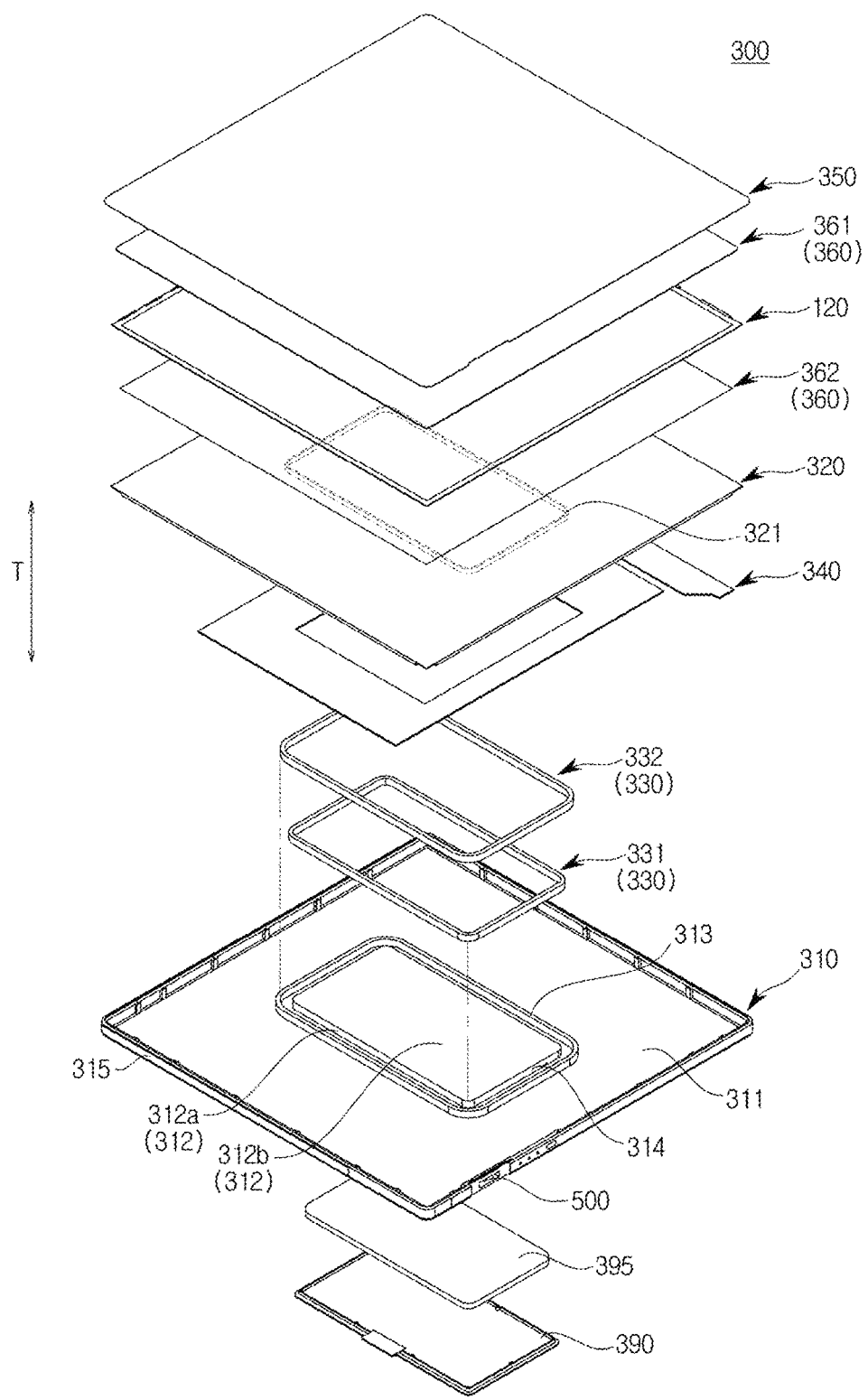
FIG. 4 illustrates an exploded view of the X-ray detector, according to the first embodiment of the present disclosure.
Figure 5:
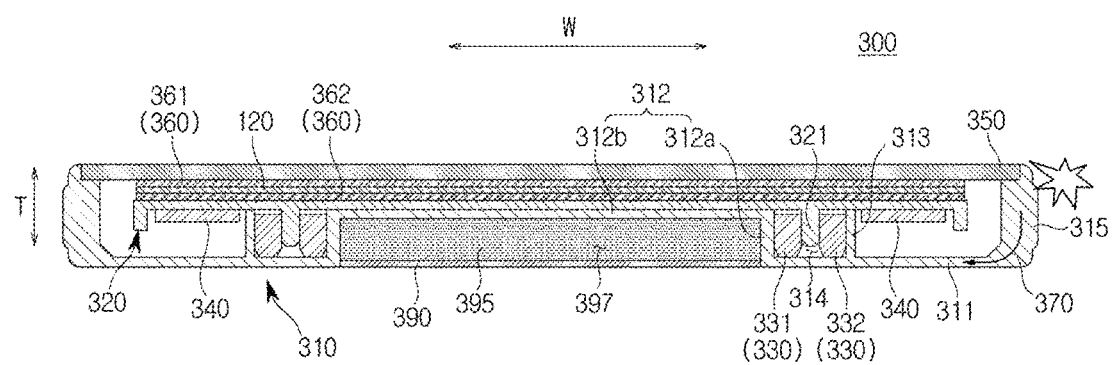
FIG. 5 illustrates a cross-sectional view of the X-ray detector of FIG. 3 cut along a line C-C'.

FIG. 3 illustrates a perspective view of an X-ray detector, according to a first embodiment of the present disclosure, and FIG. 4 illustrates an exploded view of the X-ray detector, according to the first embodiment of the present disclosure. FIG. 5 illustrates a cross-sectional view of the X-ray detector of FIG. 3 cut along a line C-C'.

As shown in FIGS. 3 to 5, the X-ray detector 300 may detect X-rays irradiated from the X-ray source 70.

The X-ray detector 300 may include a main body 310. The main body 310 may form the exterior of the X-ray detector 300. The main body 310 may be shaped like a box with one side open.

The main body 310 may include a bottom plate 311.

The bottom plate 311 may have a joining groove 314 formed thereon.

The bottom plate 311 may include an uplift part 312. The uplift part 312 may be bent toward the inner side of the X-ray detector 300 so as to form a battery receptacle 397 on the outer side of the bottom plate 311. The uplift part 312 may form a wall of the joining groove 314.

The uplift part 312 may have a shape corresponding to a battery 395.

Preferably, the uplift part 312 may be formed in the center of the bottom plate 311.

The uplift part 312 may include a vertical extension 312a extending from the bottom plate 311 to the inside of the X-ray detector 300. The vertical extension 312a may extend to the inside of the X-ray detector 300 to be in parallel with a side wall 315 of the main body 310. Furthermore, the vertical extension 312a may be spaced apart from the side wall 315 of the main body 310. The vertical extension 312a may define the sides of the uplift part 312.

The uplift part 312 may further include a horizontal extension 312b that forms the battery receptacle 397 with the vertical extension 312a. Specifically, the horizontal extension 312b and the vertical extension 312a together may form the battery receptacle 397 with one side open. The horizontal extension 312b may define the top side of the uplift part 312.

The bottom plate 311 may further include a rib 313. The rib 313 may extend to the inside of the X-ray detector 300 to be located outside the uplift part 312. The rib 313 may form another wall of the joining groove 314. Specifically, the joining groove 314 may be formed between the uplift part 312 and the rib 313. More specifically, the joining groove 314 may be formed between the vertical extension 312a of the uplift part 312 and the rib 313. From another perspective, the rib 313 may extend to the inside of the X-ray detector 300 to be spaced apart from and in parallel with the side wall 315 of the main body 310. Then, the rib 313 may form one side of the wall of the joining groove 314.

The main body 310 may further include the side wall 315. The side wall 315 may extend from the bottom plate 311 in the thickness direction T of the X-ray detector 300. The side wall 315 may be integrally formed with the bottom plate 311. The main body 310 with the side wall 315 and the bottom plate 311 integrally formed has better rigidity compared to a main body with the side wall 315 and the bottom plate 311 formed separately. Accordingly, it may effectively protect the detector panel 120 from deformation of the main body 310 from an external force.

The X-ray detector 300 may further include the detector panel 120 arranged inside the main body 310 for converting X-rays irradiated from the X-ray source 70 into an electric signal.

The detector panel 120 may be arranged on a middle block 320. That is, the detector panel 120 may be supported by the middle block 320.

The detector panel 120 may be arranged inside the main body 310 spaced apart from the main body 310. Specifically, the detector panel 120 may be arranged inside the main body 310 spaced apart at a certain distance from the bottom plate 311 and the side wall 315 of the main body 310. The reason is that if the detector panel 120 is arranged inside the main body 310 to be in contact with the main body 310, the detector panel 120 is likely to be damaged from an external shock applied to the main body 310. For example, if the detector panel 120 is arranged inside the main body 310 to come into contact with the side wall 315 of the main body 310, an external shock applied to the side wall 315 of the main body 310 may be directly delivered to the detector panel 120, thus easily damaging the detector panel 120.

The X-ray detector 300 may further include a scintillator (not shown).

The scintillator may include a fluorescent substance. The scintillator may convert incident X-rays to visible rays. A cover (not shown) may be attached onto one side of the scintillator to protect the scintillator. The scintillator may be formed of a metal, such as aluminum.

The X-ray detector 300 may further include the middle block 320.

The middle block 320 may be equipped inside the main body 310 to support the detector panel 120. The middle block 320 may include a boss 321. The boss 321 may be formed to protrude toward the bottom plate 311 of the main body 310 to be inserted into the joining groove 314.

The middle block 320 may be supported on the uplift part 312. Specifically, the middle block 320 may be arranged on the horizontal extension 312b of the uplift part 312.

The middle block 320 may be arranged inside the main body 310 spaced apart from the main body 310. Specifically, the middle block 320 may be arranged inside the main body 310 spaced apart from the side wall 315 of the main body 310.

The X-ray detector 300 may further include a buffer member 330. The buffer member 330 may be arranged in the main body 310 to block external shocks from being delivered to the detector panel 120.

The buffer member 330 may be placed in at least part of the joining groove 314 to prevent the boss 321 of the middle block from coming into contact with the joining groove 314.

The buffer member 330 may include a first buffer member 331 arranged along the girth of the uplift part 312. Specifically, the first buffer member 331 may be arranged along the girth of the vertical extension 312a of the uplift part 312. The first buffer member 331 may be positioned tightly against the uplift part 312 to enclose the girth of the vertical extension 312a of the uplift part 312.

The buffer member 330 may further include a second buffer member 332 arranged along the girth of the rib 313. Specifically, the second buffer member 332 may be arranged along the girth of the rib 313 to be positioned inside the joining groove 314. The second buffer member 332 may face the boss 321. The second buffer member 332 may be arranged tightly against the rib 313.

While it has thus far been assumed that there are multiple buffer members 330, it is possible to arrange a single buffer member 330 in the joining groove 314.

The buffer member 330 may have the form of a closed loop. The second buffer member 332 may have the form of a more expanded closed loop than that of the first buffer member 331. The form of the buffer member 330 is not, however, limited to the closed loop, but may be modified in various ways.

The buffer member 330 may be formed of an elastic material. For example, the buffer member 330 may be formed of silicon, rubber, etc.

An external force applied to the X-ray detector 300 may move the middle block 320. In this case, the buffer member 330 may prevent the boss 321 of the middle block 320 from directly coming into contact with the joining groove 314 due to the movement of the middle block 320. Furthermore, the buffer member 330 may restrict the movement of the middle block 320 in the width direction W of the X-ray detector 300 to prevent the middle block 320 from coming into contact or colliding with the side wall 315 of the main body 310. In this way, the buffer member 330 may prevent external shocks applied to the main body 310 from being directly delivered to the detector panel 120 arranged on the middle block 320 by preventing direct contact between the middle block 320 and the main body 310.

The X-ray detector 300 may further include a circuit board 340.

The circuit board 340 uses data obtained based on signals read by the detector panel 120 to perform an operation to obtain an image of the object. The circuit board 340 may be received inside the X-ray detector 300 to control an operation of the X-ray detector 300. In other words, the circuit board 340 may be received inside the main body 310. For example, the circuit board 340 may be equipped on the middle block 320. Specifically, the circuit board 340 may be mounted on one side of the middle block 320 opposite to the bottom plate 311 of the main body 310. The circuit board 340 may include a memory and a processor. The memory may store information about shadows of the object at respective X-ray radiation angles, and the processor may calculate an X-ray radiation angle based on the shape of a shadow of the object formed on the detector panel 120 and the shadow information in the memory. The memory and the processor may be arranged outside of the X-ray detector 300.

The detector panel 120 and the circuit board 340 may be connected electrically.

The X-ray detector 300 may further include a main body cover 350. The main body cover 350 may be mounted on one open side of the main body 310. The main body cover 350 may have the form of e.g., a carbon plate. A deco sheet (not shown) may further be included on one side of the main body cover 350.

The X-ray detector 300 may further include a cushion member 360. The cushion member 360 may be arranged on the detector panel 120 to protect the detector panel 120 from external shocks.

The cushion member 360 may include a sponge.

The cushion member 360 may include a first cushion member 361 arranged between the detector panel 120 and the main body cover 350. The cushion member 360 may further include a second cushion member 362 arranged between the detector panel 120 and the middle block 320.

The X-ray detector 300 may further include the battery 395. The battery 395 may be detachably received in the battery receptacle 397.

The X-ray detector 300 may further include a battery cover 390. The battery cover 390 may be detachably combined with the bottom plate 311 of the main body 310 to open/close the battery receptacle 397.

The X-ray detector 300 may further include a terminal 500 to which a coupling module (not shown) is coupled. The terminal 500 may be equipped in the X-ray detector 300 so that the coupling module is coupled. In other words, the terminal 500 may be equipped in the X-ray detector 300 so that the coupling module electrically connected to the circuit board 340 is coupled. That is, the coupling module may be electrically connected to the circuit board 340 by being coupled with the terminal 500. Specifically, the terminal 500 may be formed on the side wall 315 of the main body 310.

The X-ray detector 300 may further include a shock transfer path 370.

The shock transfer path 370 is a path for external shocks to be transferred, and may be formed along the side wall 315 and the bottom plate 311 of the main body 310.

The buffer member 330 may be arranged in the shock transfer path 370 to prevent external shocks from being delivered to the detector panel 120. The buffer member 330 may effectively protect the detector panel 120 by blocking out shocks transferred along the shock transfer path 370 from the main body 310.

The shock transfer path 370 will now be described from another perspective. Edges of the detector panel 120 are typically vulnerable to external shocks. That is, if an external shock is delivered to the edge of the detector panel 120, the detector panel 120 may be more likely to be damaged. Accordingly, given that the shock transfer path 370 is defined as a path for external shocks applied to the main body 310 to be transferred toward the detector panel 120, it is desirable to design the shock transfer path 370 to be as long as possible. The reason is that if the shock transfer path 370 is long, the external shock applied to the main body 310 is most likely to dissipate while being transferred in the long shock transfer path 370. To secure the long shock transfer path 370, the detector panel 120 may be arranged inside the main body 310 spaced apart from the main body 310.

Furthermore, it is desirable to design the shock transfer path 370 for external shocks to be transferred not to the edge but to the center of the detector panel 120. This is because the center of the detector panel 120 is less vulnerable to impact than the edge of the detector panel 120. As shown in FIG. 5, with the bottom plate 311 and the middle block 320 of the main body 310, external shocks may be prevented from being delivered to the edge of the detector panel 120. For example, if an external shock is applied to the side wall 315 of the main body 310, the external shock is delivered to the bottom plate 311 of the main body 310 from the side wall 315 of the main body 310 along the shock transfer path 370. In this regard, the majority of the external shock is absorbed by the buffer member 330 arranged in the shock transfer path 370. Part of the shock, which is not absorbed by the buffer member 330, reaches the uplift part 312 of the bottom plate 311 through the buffer member 330. Since the uplift part 312, the horizontal extension 312b in particular, is arranged to come into direct contact with the middle block 320, the shock reaches the detector panel 120 arranged on the middle block 320 through the middle block 320. In this case, since the uplift part 312 is formed in the center of the bottom plate 311, the shock reaches not the edge but the center of the detector panel 120. That is, preventing the shock from being delivered to the edge of the detector panel 120 earlier than the center of the detector panel 120 may effectively protect the detector panel 120.

Figure 6:
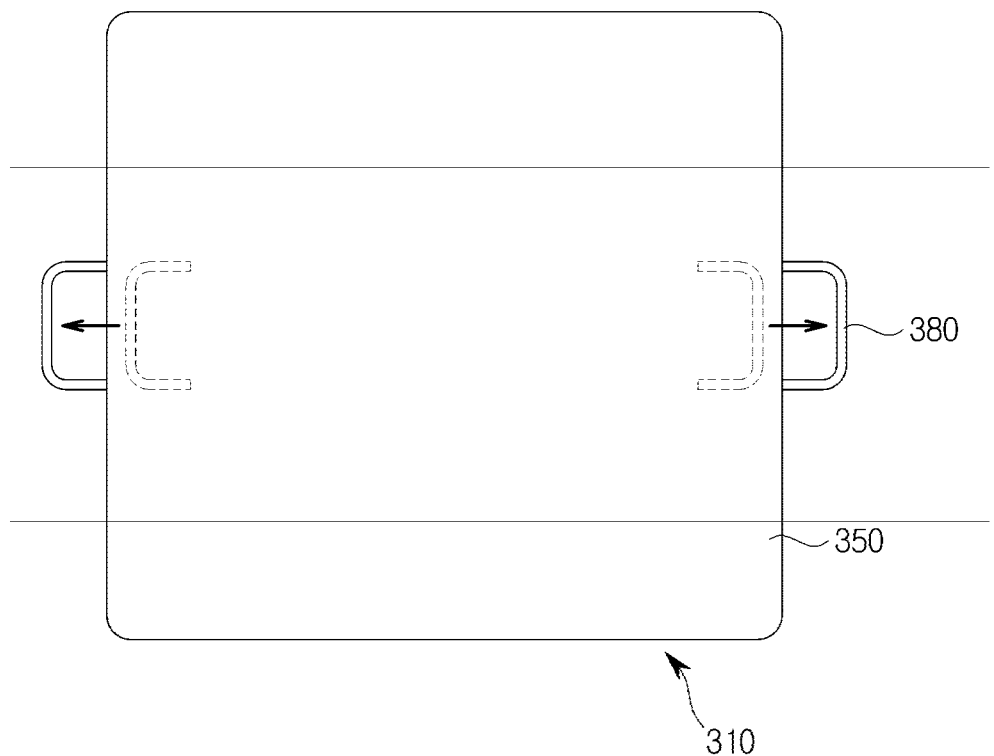
FIG. 6 illustrates a schematic diagram for explaining how a handle in the X-ray detector operates, according to the first embodiment of the present disclosure.

FIG. 6 illustrates a schematic diagram for explaining how a handle in the X-ray detector operates, according to the first embodiment of the present disclosure. Reference numerals not shown may be referred to from FIGS. 3 to 5.

Referring to FIG. 6, the X-ray detector 300 may further include at least one handle 380. The at least one handle 380 may be installed in the main body 310. Specifically, the at least one handle 380 may be installed on the side wall 315 of the main body 310.

The at least one handle 380 may be installed in the main body 310 to be pushed into or pulled out of the main body 310. The at least one handle 380 may be formed to remain pushed inside the main body 310 in ordinary times, and to be pulled by the user out of the main body 310 to be used as necessary. The at least one handle 380 may be installed in the main body 310 to be able to slide.

As such, the X-ray detector 300 may employ the at least one handle 380 that may be built into the main body 310, to prevent the X-ray detector 300 from falling, thereby minimizing damage to the X-ray detector 300.

Figure 7:
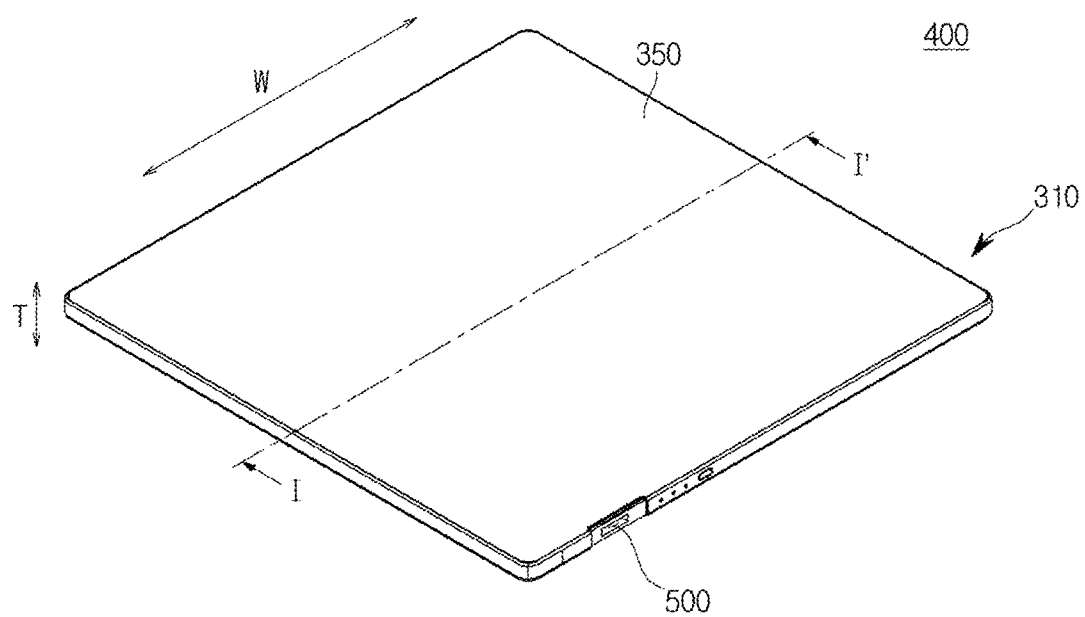
FIG. 7 illustrates a perspective view of an X-ray detector, according to a second embodiment of the present disclosure.
Figure 8:
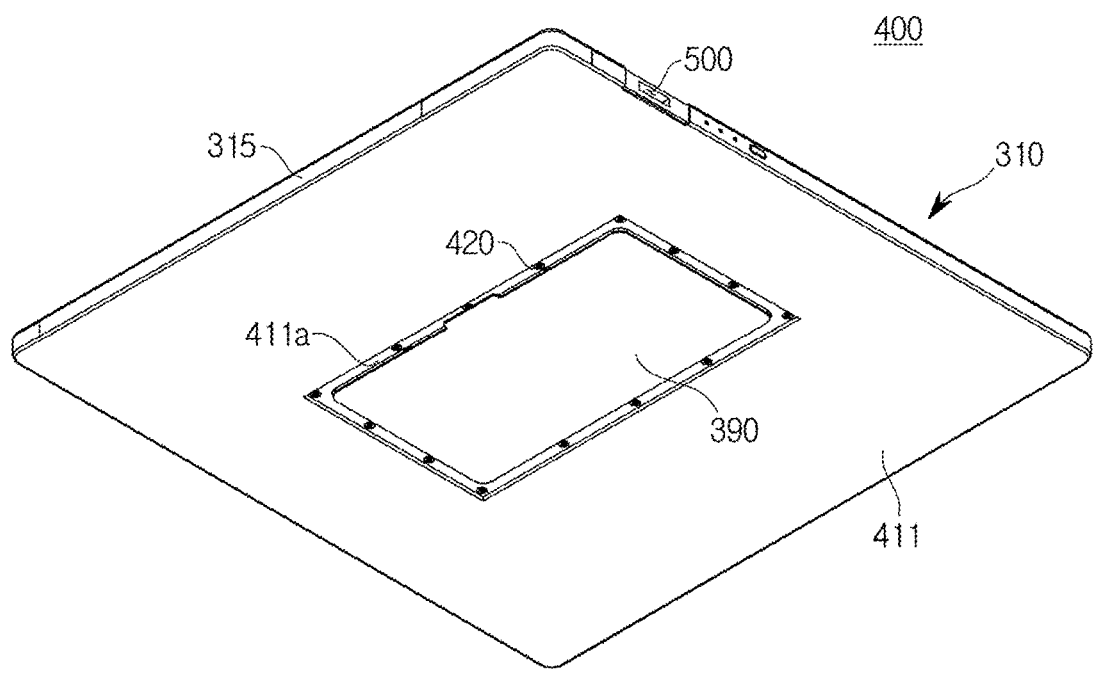
FIG. 8 illustrates a perspective view of the X-ray detector viewed at an angle different from that of FIG. 7, according to the second embodiment of the present disclosure.
Figure 9:
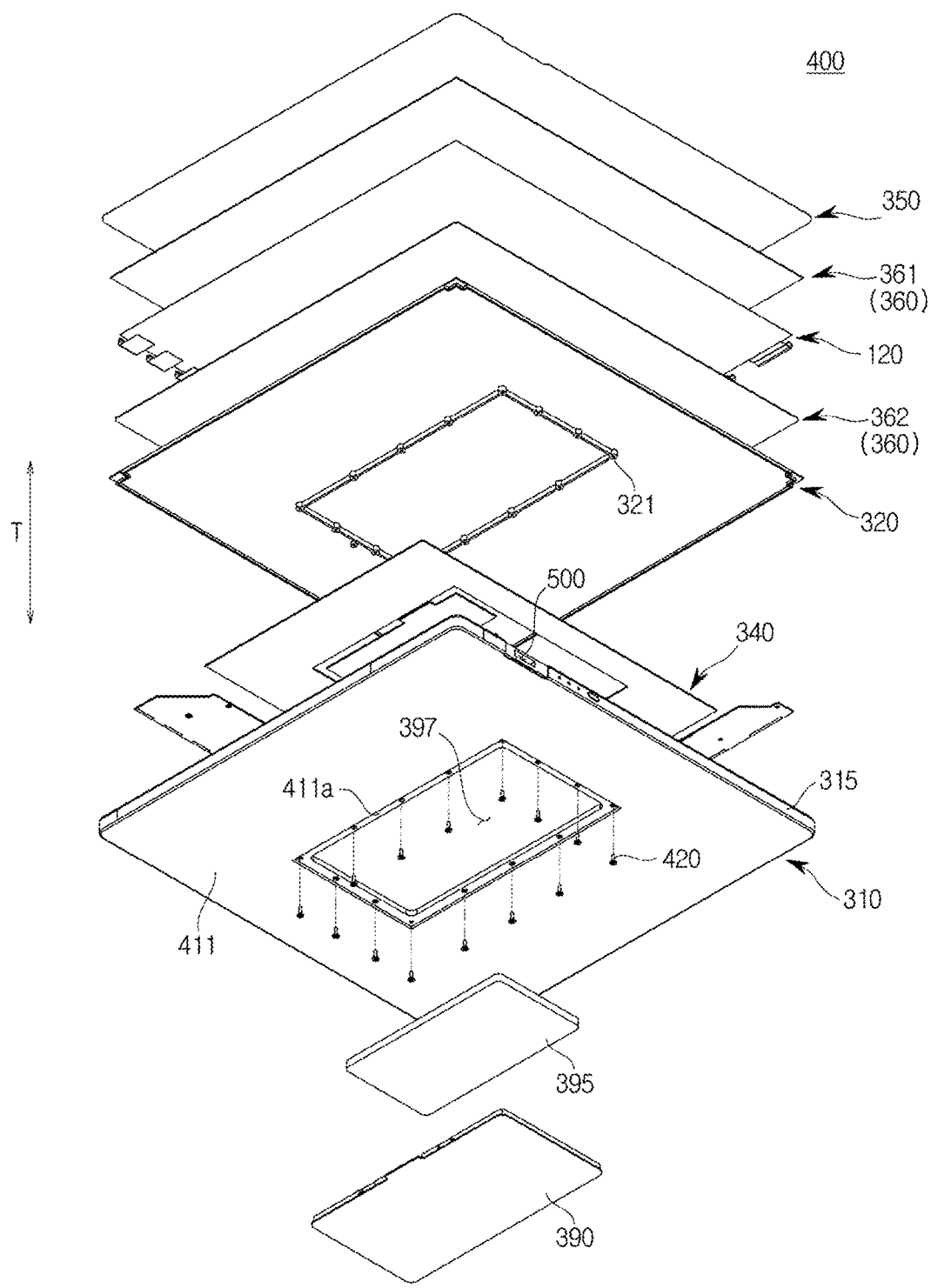
FIG. 9 illustrates an exploded view of the X-ray detector, according to the second embodiment of the present disclosure.
Figure 10:
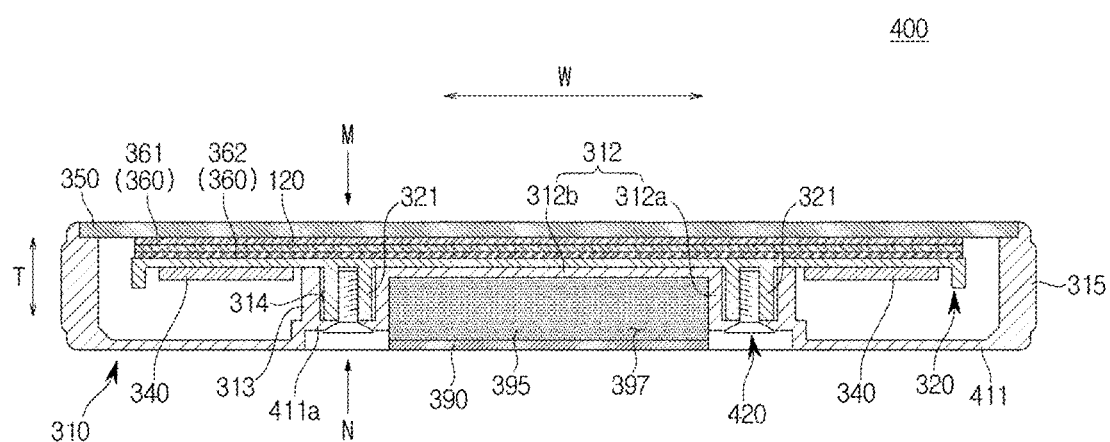
FIG. 10 illustrates a cross-sectional view of the X-ray detector of FIG. 7 cut along a line I-I'.

FIG. 7 illustrates a perspective view of an X-ray detector, according to a second embodiment of the present disclosure, and FIG. 8 illustrates a perspective view of the X-ray detector viewed at an angle different from that of FIG. 7, according to the second embodiment of the present disclosure. FIG. 9 illustrates an exploded view of the X-ray detector, according to the second embodiment of the present disclosure, and FIG. 10 illustrates a cross-sectional view of the X-ray detector of FIG. 7 cut along a line I-I'. The same components as those shown in FIGS. 3 to 5 are allocated the same reference numerals as in FIGS. 3 to 5. Descriptions overlapping those of FIGS. 3 to 5 will be omitted herein.

As shown in FIGS. 7 to 10, an X-ray detector 400 may include the main body 310. The main body 310 may be shaped like a box with one side open.

The main body 310 may include a bottom plate 411.

The bottom plate 411 may have the joining groove 314 formed thereon.

The bottom plate 411 may include the uplift part 312 bent toward the inside of the X-ray detector 400 so as to form the battery receptacle 397 on the outer surface of the bottom plate 411. The uplift part 312 may form a wall of the joining groove 314.

The bottom plate 411 may further include the rib 313. The rib 313 may extend to the inside of the X-ray detector 400 to be located outside of the uplift part 312. The rib 313 may form another wall of the joining groove 314.

The bottom plate 411 may further include a groove 411a formed along the edge of the battery receptacle 397. The groove 411a may be formed along the edge of the battery receptacle 397 to be located outside of the battery receptacle 397. The groove 411a may have a shape in which the bottom plate 411 is sunk into the X-ray detector 400. The extent of sinking of the groove 411a may be smaller than that of the battery receptacle 397.

The main body 310 may further include the side wall 315 that extends in the thickness direction T of the X-ray detector 400.

The X-ray detector 400 may further include the detector panel 120 received inside the main body 310 for converting X-rays into electric signals. The detector panel 120 may be received inside the main body 310 spaced apart from the main body 310.

The X-ray detector 400 may further include the middle block 320 received inside the main body 310 for the detector panel 120 to be safely placed. The middle block 320 may be received inside the main body 310 while being separated from the main body 310. Specifically, the middle block 320 may be received inside the main body 310 to be spaced apart from the side wall 315 of the main body 310. The middle block 320 may include a boss 321 that protrudes toward the bottom plate 411 of the main body 310 to be inserted into the joining groove 314.

The X-ray detector 400 may further include a battery cover 390. The battery cover 390 may be detachably combined with the bottom plate 411 of the main body 310 to open/close the battery receptacle 397.

The X-ray detector 400 may further include a fixing member 420.

The fixing member 420 may serve to fix the middle block 320 onto the bottom plate 411 of the main body 310. Specifically, the fixing member 420 may be combined onto the bottom plate 411 in a direction N opposite to a direction M in which the boss 321 is inserted to the joining groove 314, in order to prevent movement of the middle block 320.

The fixing member 420 may be combined into the groove 411a of the bottom plate 411 to fix the middle block 320 onto the bottom plate 411.

The fixing member 420 may pass through the bottom plate 411, especially the groove 411a, and may be combined with the boss 321 of the middle block 320.

The fixing member 420 may include a screw without being limited thereto.

As such, in the case that the middle block 320 is fixed onto the bottom plate 411 with the fixing member 420, even if an external shock is applied to the X-ray detector 400, the motion of the middle block 320 in the width direction W of the X-ray detector 400 is suppressed, thereby preventing contact or collision of the middle block 320 against the side wall 315 of the main body 310. That is, the detector panel 120 arranged on the middle block 320 may be effectively protected by fixing the middle block 320 onto the bottom plate 411 with the fixing member 420 to minimize an external shock delivered to the middle block 320.

Figure 11:
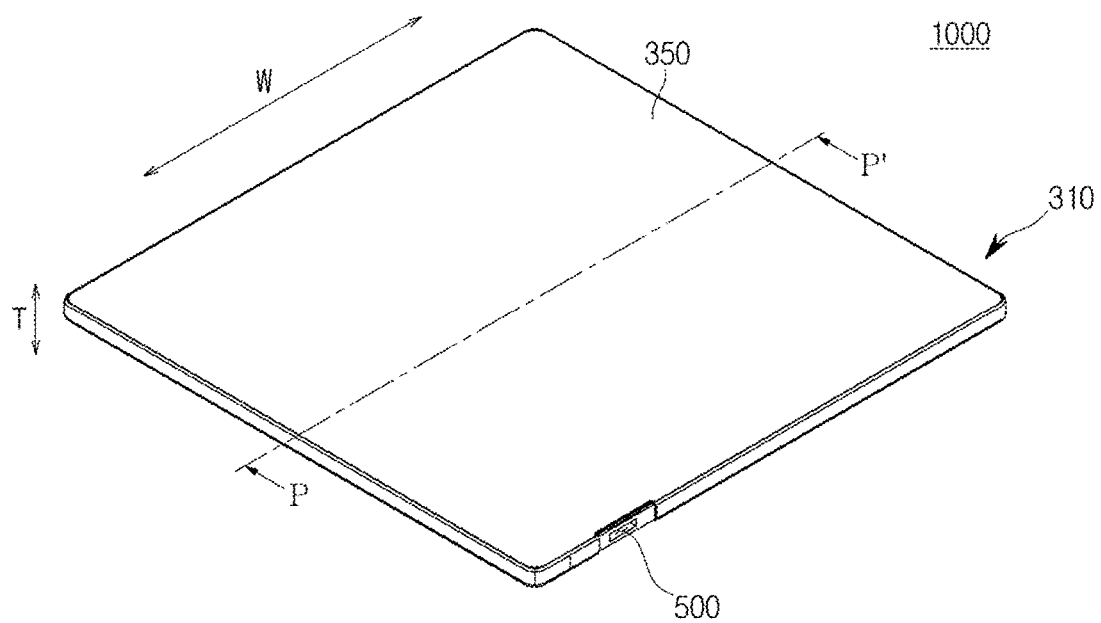
FIG. 11 illustrates a perspective view of an X-ray detector, according to a third embodiment of the present disclosure.
Figure 12:
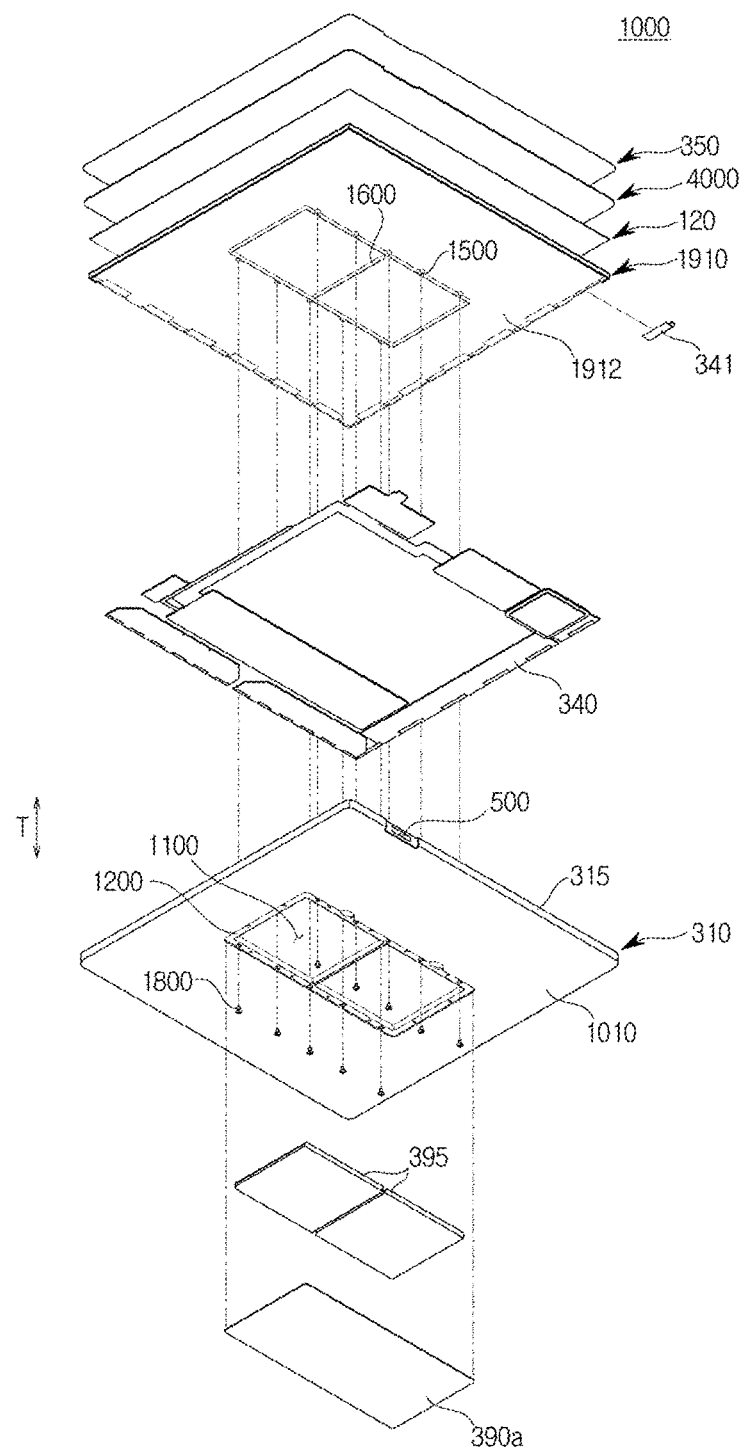
FIG. 12 illustrates an exploded view of the X-ray detector, according to the third embodiment of the present disclosure.
Figure 13:
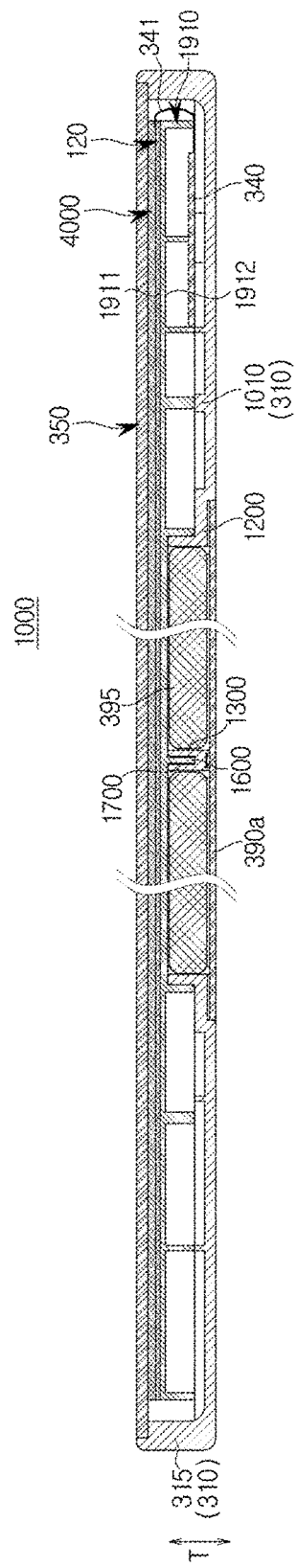
FIG. 13 illustrates a cross-sectional view of the X-ray detector of FIG. 11 cut along a line P-P'.
Figure 14:
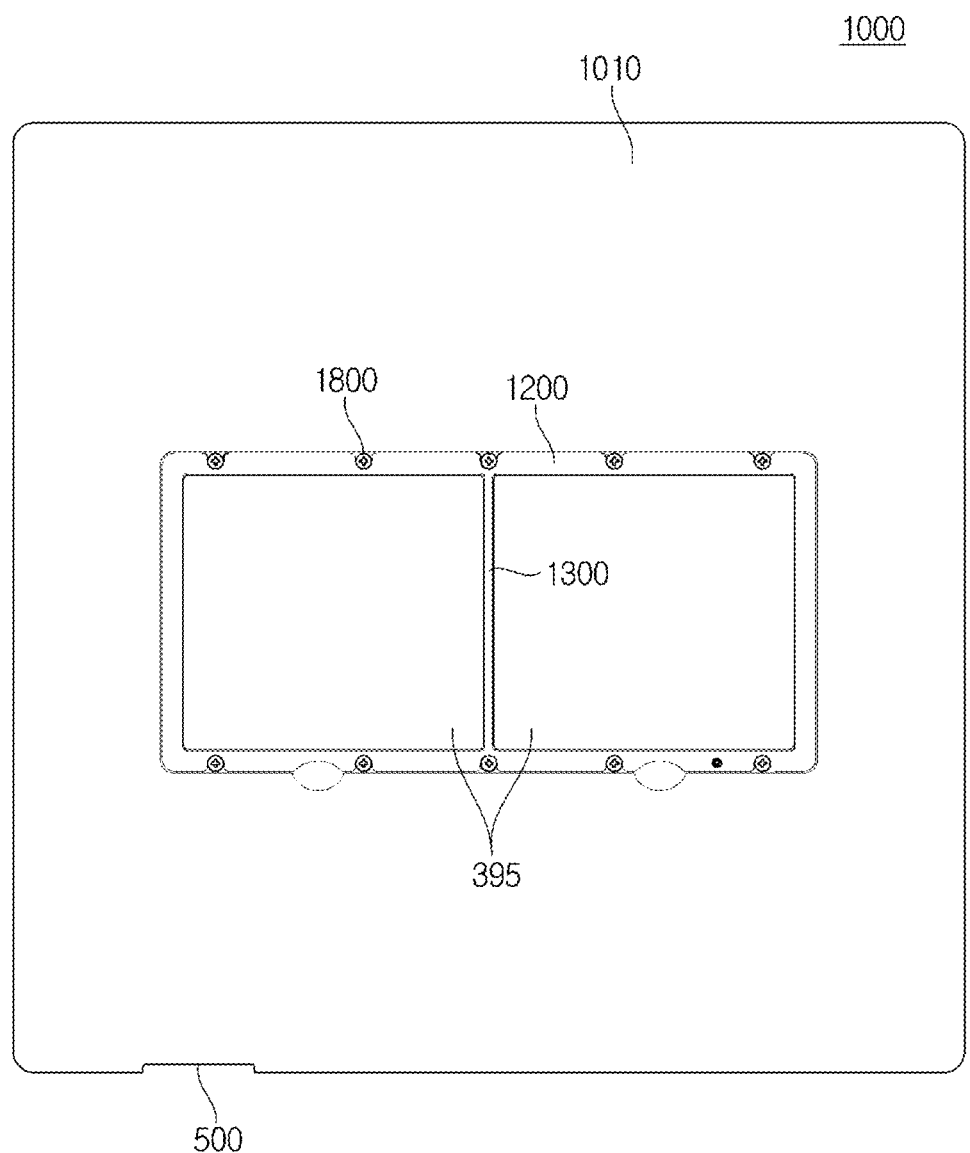
FIG. 14 illustrates a bottom view of the X-ray detector, according to the third embodiment of the present disclosure.
Figure 15:
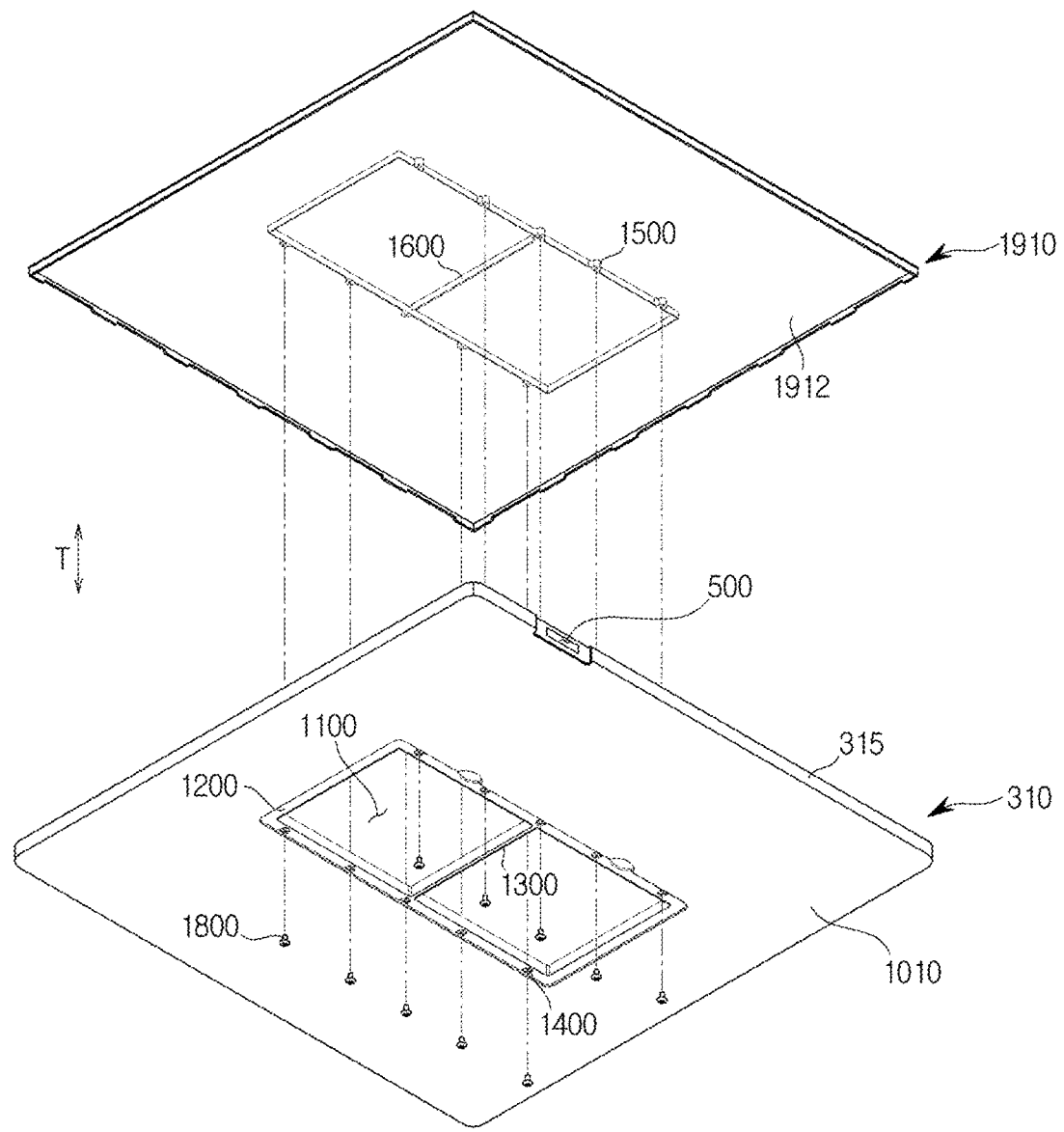
FIG. 15 illustrates a view of the X-ray detector showing a state in which a middle block and a main body are separate from each other, according to the third embodiment of the present disclosure.

FIG. 11 illustrates a perspective view of an X-ray detector, according to a third embodiment of the present disclosure, and FIG. 12 illustrates an exploded view of the X-ray detector, according to the third embodiment of the present disclosure. FIG. 13 illustrates a cross-sectional view of the X-ray detector of FIG. 11 cut along a line P-P', and FIG. 14 illustrates a bottom view of the X-ray detector, according to the third embodiment of the present disclosure. FIG. 15 illustrates a view of the X-ray detector showing a state in which a middle block and a main body are separate from each other, according to the third embodiment of the present disclosure. Hereinafter, reference numerals not shown refer to a description of the X-ray detector 300, according to the first embodiment of the present disclosure. In FIG. 14, a battery cover 390a may be omitted.

As shown in FIGS. 11 to 15, an X-ray detector 1000 may be provided to detect the X-rays irradiated from the X-ray source 70.

The X-ray detector 1000 may include the main body 310. The main body 310 may form the exterior of the X-ray detector 1000. The main body 310 may be shaped like a box with one side open.

The main body 310 may include a bottom plate 1010.

The main body 310 may further include the side wall 315. The side wall 315 may extend from the bottom plate 1010 in the thickness direction T of the X-ray detector 1000. The side wall 315 may be integrally formed with the bottom plate 1010. The main body 310 with the side wall 315 and the bottom plate 1010 integrally formed has better rigidity compared to a main body with the side wall 315 and the bottom plate 1010 formed separately. Accordingly, it may effectively protect the detector panel 120 from deformation of the main body 310 from an external force.

The main body 310 may further include a battery receptacle 1100. The battery receptacle 1100 may be formed in the bottom plate 1010 of the main body 310 so that the battery 395 could be accommodated. Specifically, the battery receptacle 1100 may be formed at a central portion of the bottom plate 1010 of the main body 310. That is, the battery receptacle 1100 may be formed in the bottom plate 1010 of the main body 310 so as to be spaced apart from an edge of the bottom plate 1010 by a predetermined distance inward of the bottom plate 1010. The battery receptacle 1100 may be defined by the bottom plate 1010 of the main body 310 and a middle block 1910 to be described later.

The main body 310 may further include a battery receptacle frame 1200. The battery receptacle frame 1200 may be formed in the bottom plate 1010 of the main body 310 along the circumference of the battery receptacle 1100. That is, the battery receptacle frame 1200 may be formed in the bottom plate 1010 of the main body 310 along an outer edge of the battery receptacle 1100. The battery receptacle frame 1200 may be recessed from the bottom plate 1010 of the main body 310 to have a predetermined depth. The battery cover 390a to be described later may be coupled to the battery receptacle frame 1200.

The main body 310 may further include a partition 1300. The partition 1300 may be formed in the bottom plate 1010 of the main body 310 to partition the battery receptacle 1100 into a plurality of spaces. As an example, the partition 1300 may be formed in the bottom plate 1010 of the main body 310 to partition the battery receptacle 1100 into two spaces. One end of the partition 1300 may be connected to one side of the battery receptacle frame 1200 facing each other and the other end of the partition 1300 may be connected to the other side of the battery receptacle frame 1200 facing each other. The partition 1300 may divide the battery receptacle 1100 into a plurality of spaces having the same size or a plurality of spaces having different sizes. The number and size of the plurality of spaces of the battery receptacle 1100 partitioned by the partition 1300 may correspond to the number and size of the plurality of batteries accommodated in the plurality of spaces.

The main body 310 may further include a plurality of guide holes 1400. The plurality of guide holes 1400 may be formed in the bottom plate 1010 of the main body 310 along the circumference of the battery receptacle 1100. Specifically, the plurality of guide holes 1400 may be formed in the battery receptacle frame 1200 to guide an engagement position of a plurality of fixing members 1800 to be described later. The plurality of fixing members 1800 may be coupled to a plurality of bosses 1500 formed in the middle block 1910 through the plurality of guide holes 1400. The plurality of guide holes 1400 may be formed to be spaced apart from each other. The plurality of guide holes 1400 may have a hole shape with one side opened. However, a shape of the plurality of guide holes 1400 is not limited to the above-described example, and may be variously changed. As an example, the plurality of guide holes 1400 may have various shapes such as a circular shape, an elliptical shape, and a polygonal shape.

The X-ray detector 1000 may further include the detector panel 120 provided inside the main body 310 for converting X-rays irradiated from the X-ray source 70 into electric signals.

The detector panel 120 may be disposed on the middle block 1910. That is, the detector panel 120 may be supported by the middle block 1910. As an example, the detector panel 120 may be bonded onto the middle block 1910 by an adhesive member such as a double-sided tape or the like.

The detector panel 120 may be disposed inside the main body 310 so as to be spaced apart from the main body 310. Specifically, the detector panel 120 may be disposed inside the main body 310 to be spaced apart from the bottom plate 1010 and the side wall 315 of the main body 310. This is because when the detector panel 120 is disposed inside the main body 310 to be in contact with the main body 310, there is a risk that the detector panel 120 is damaged due to an external impact applied to the main body 310. As an example, when the detector panel 120 is disposed inside the main body 310 in contact with the side wall 315 of the main body 310, the external impact applied to the side wall 315 of the main body 310 may be directly transmitted to the detector panel 120. Therefore, the detector panel 120 may be easily damaged.

The X-ray detector 1000 may further include a scintillator 4000. The scintillator 4000 may include a fluorescent substance. The scintillator 4000 may convert incident X-rays into visible rays. A cover (not shown) for protecting the scintillator 4000 may be disposed on one surface of the scintillator 4000. The scintillator 4000 may be formed of a metal, such as aluminum. The scintillator 4000 may be disposed on the detector panel 120 so as to face the main body cover 350.

The X-ray detector 1000 may further include the middle block 1910. The middle block 1910 may be disposed inside the main body 310 to support the detector panel 120.

The middle block 1910 may include a first surface 1911 facing the detector panel 120 and a second surface 1912 facing the bottom plate 1010 of the main body 310. The detector panel 120 may be seated on the first surface 1911 of the middle block 1910. The circuit board 340 to be described later may be fixedly coupled on the second surface 1912 of the middle block 1910.

The middle block 1910 may define the battery receptacle 1100 together with the bottom plate 1010 of the main body 310. Specifically, the second surface 1912 of the middle block 1910 may define the battery receptacle 1100 together with the bottom plate 1010 of the main body 310.

The middle block 1910 may further include the plurality of bosses 1500. The plurality of bosses 1500 may be formed to protrude from the second surface 1912 of the middle block 1910. The plurality of bosses 1500 may be formed along the circumference of the battery receptacle 1100 to correspond to the plurality of guide holes 1400. The plurality of fixing members 1800 may be coupled to the plurality of bosses 1500. Specifically, the plurality of fixing members 1800 may be fixedly coupled to the plurality of bosses 1500 through the plurality of guide holes 1400. The middle block 1910 may be fixedly coupled to the main body 310 by the plurality of fixing members 1800.

The middle block 1910 may further include a rib 1600. The rib 1600 may be formed in the middle block 1910 to correspond to the partition 1300 of the main body 310. The rib 1600 may divide the battery receptacle 1100 into a plurality of spaces together with the partition 1300 of the main body 310. The rib 1600 may be formed to protrude from the second surface 1912 of the middle block 1910. The rib 1600 may be coupled to the partition 1300. Specifically, the rib 1600 may be coupled to a rib engagement groove 1700 formed in the partition 1300. The rib engagement groove 1700 may be recessed in the partition 1300 so that the rib 1600 is engaged.

The X-ray detector 1000 may further include the plurality of fixing members 1800 that couple the middle block 1910 and the main body 310 together. The plurality of fixing members 1800 may be fixedly coupled to the plurality of bosses 1500 formed in the middle block 1910 through the plurality of guide holes 1400. The middle block 1910 may be fixed to the main body 310 through an engagement between the plurality of fixing members 1800 and the plurality of bosses 1500. Specifically, the middle block 1910 may be fixed to the bottom plate 1010 of the main body 310 through the engagement between the plurality of fixing members 1800 and the plurality of bosses 1500. The plurality of fixing members 1800 may include a screw, but a type of the plurality of fixing members 1800 is not limited to the screw.

The X-ray detector 1000 may further include the circuit board 340. The circuit board 340 uses data obtained based on signals read by the detector panel 120 to perform an operation to obtain an image of the object. The circuit board 340 may be received inside the X-ray detector 1000 to control an operation of the X-ray detector 1000. In other words, the circuit board 340 may be received inside the main body 310. For an example, the circuit board 340 may be equipped on the middle block 320. Specifically, the circuit board 340 may be mounted on the second surface 1912 of the middle block 320. The circuit board 340 may include a memory and a processor. The memory may store information about shadows of the object at respective X-ray radiation angles, and the processor may calculate an X-ray radiation angle based on the shape of a shadow of the object formed on the detector panel 120 and the shadow information in the memory. The memory and the processor may be arranged outside of the X-ray detector 1000.

The X-ray detector 1000 may further include a flexible circuit board 341 for electrically connecting the detector panel 120 and the circuit board 340.

The X-ray detector 1000 may further include the main body cover 350. The main body cover 350 may be mounted on one open side of the main body 310. The main body cover 350 may have the form of e.g., a carbon plate. A deco sheet (not shown) may further be included on one side of the main body cover 350.

The X-ray detector 1000 may further include the battery 395. The battery 395 may be detachably received in the battery receptacle 397. The X-ray detector 1000 may include at least one battery 395.

The X-ray detector 1000 may further include the battery cover 390a. The battery cover 390a may be detachably coupled to the bottom plate 1010 of the main body 310 to open or close the battery receptacle 1100. Specifically, the battery cover 390a may be detachably coupled to the battery receptacle frame 1200 of the main body 310 to open or close the battery receptacle 1100.

The X-ray detector 1000 may further include the terminal 500 to which a coupling module (not shown) is coupled. The terminal 500 may be equipped in the X-ray detector 1000 so that the coupling module is coupled. In other words, the terminal 500 may be equipped in the X-ray detector 1000 so that the coupling module electrically connected to the circuit board 340 is coupled. That is, the coupling module may be electrically connected to the circuit board 340 by being coupled with the terminal 500. Specifically, the terminal 500 may be formed on the side wall 315 of the main body 310.

When an external force is applied to the X-ray detector 1000, a movement of the middle block 1910 may occur. The plurality of fixing members 1800 may prevent the movement of the middle block 1910 primarily by engaging the middle block 1910 with the main body 310. The rib 1600 may prevent the movement of the middle block 1910 by coupling the middle block 1910 to the main body 310 through an engagement with the partition 1300. By implementing a structure that prevents the movement of the plurality of middle blocks 1910 in the X-ray detector 1000, it is possible to effectively prevent the middle block 1910 from moving when an external force is applied to the X-ray detector 1000. It is also possible to prevent a movement of the detector panel 120 disposed on the middle block 1910 and moving integrally with the middle block 1910. Therefore, damage of the detector panel 120, which could occur when the detector panel 120 collides with the main body 310, may be minimized.

Figure 16:
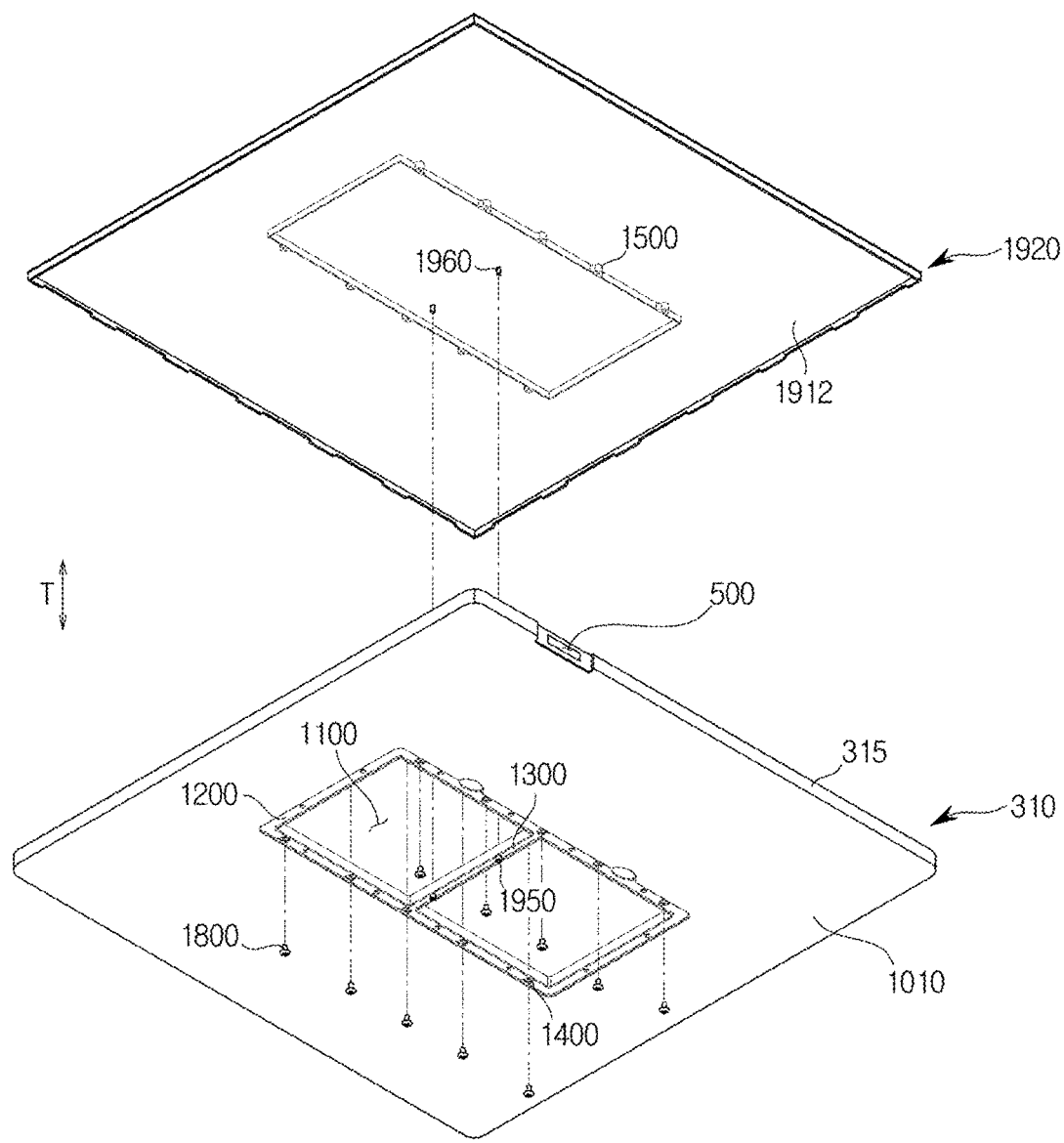
FIG. 16 illustrates a view of an X-ray detector showing a state in which a middle block and a main body are separate from each other, according to a fourth embodiment of the present disclosure.
Figure 17A:
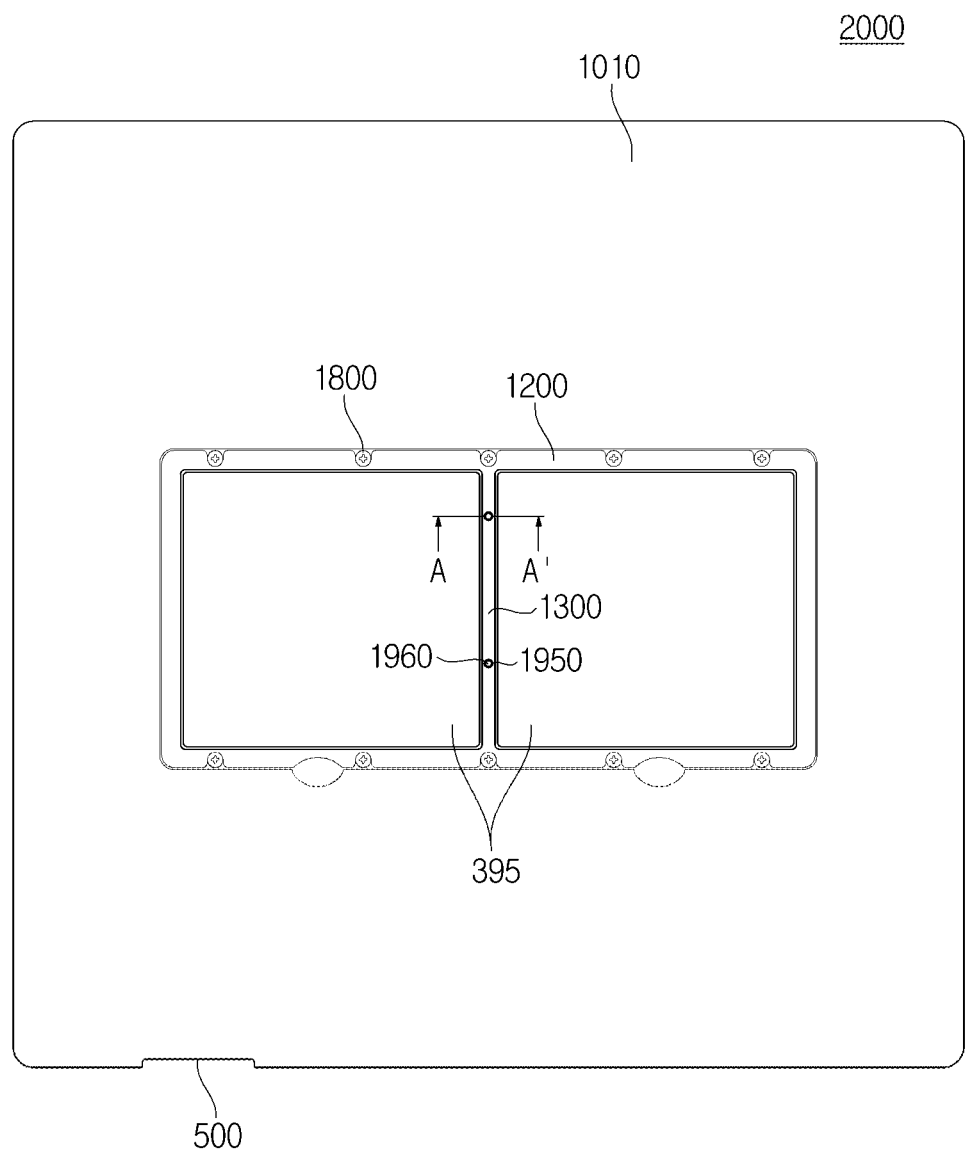
FIGS. 17A to 17C illustrate bottom views showing cases in which various structures for preventing a movement of the middle block are applied, according to the fourth embodiment of the present disclosure.
Figure 17B:
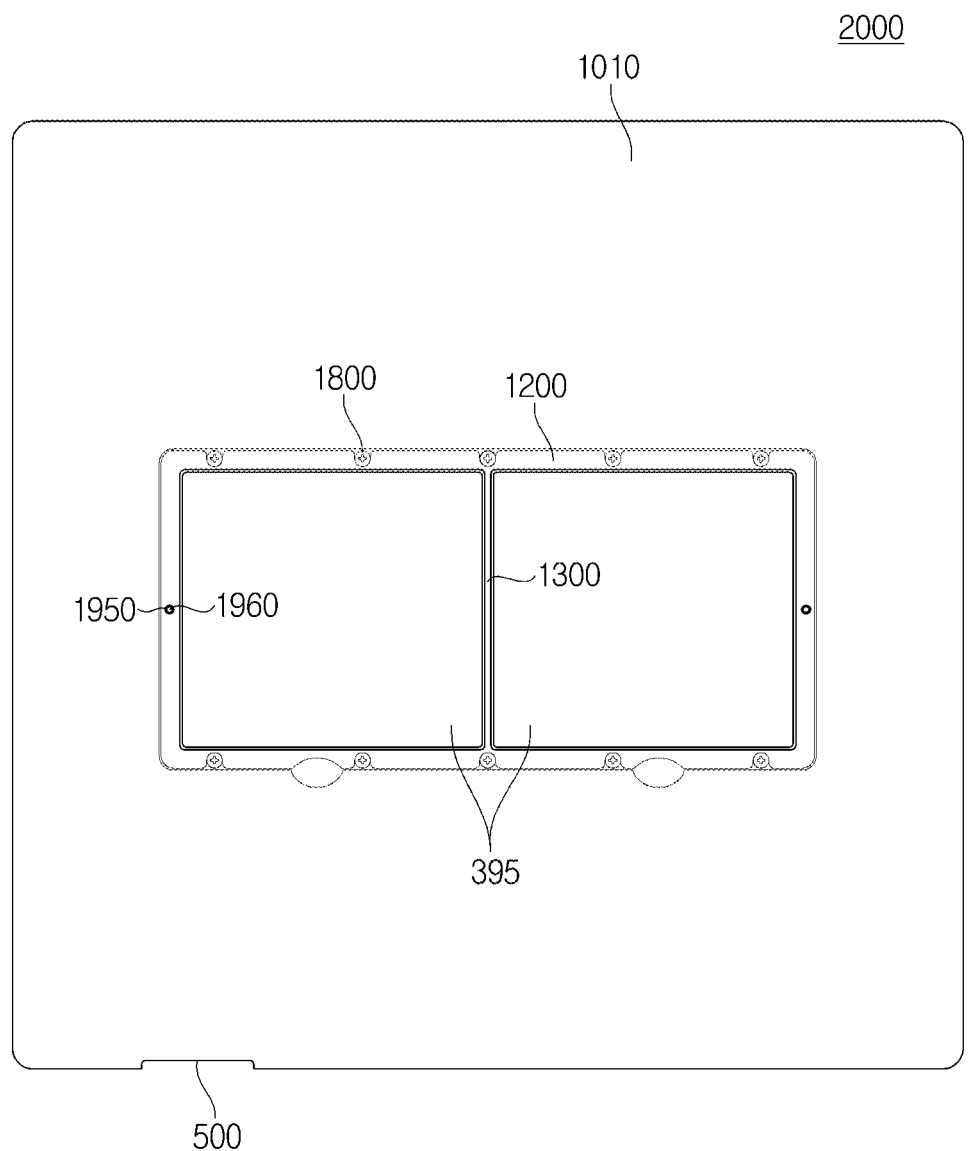
Figure 17C:
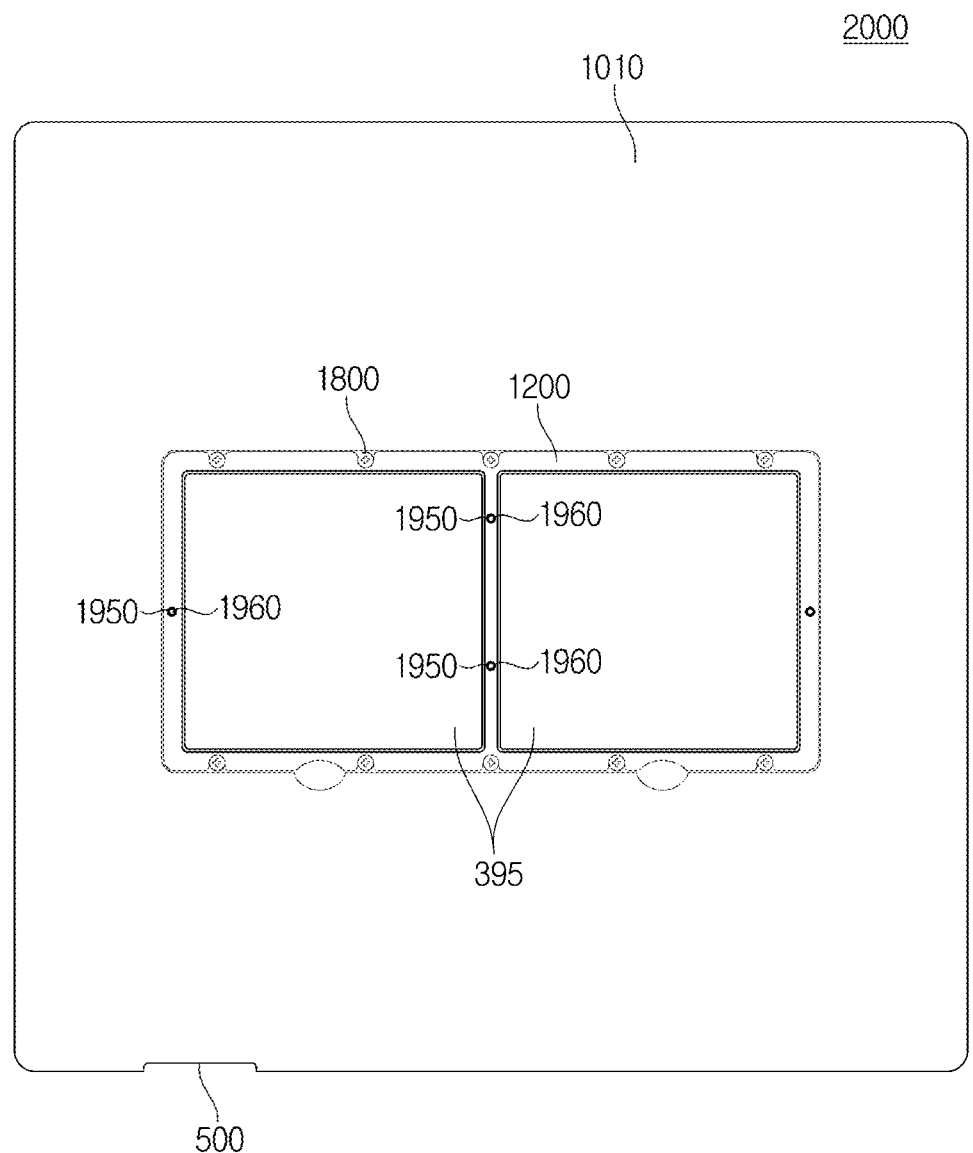
Figure 18:
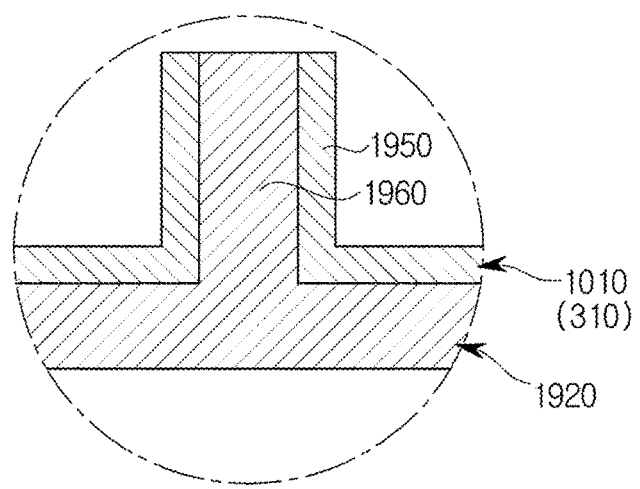
FIG. 18 illustrates a cross-sectional view of a part of the X-ray detector of FIG. 17A cut along a line A-A'.

FIG. 16 illustrates a view of an X-ray detector showing a state in which a middle block and a main body are separate from each other, according to a fourth embodiment of the present disclosure, and FIGS. 17A to 17C illustrate bottom views showing cases in which various structures for preventing a movement of a middle block are applied, according to the fourth embodiment of the present disclosure. FIG. 18 illustrates a cross-sectional view of a part of the X-ray detector of FIG. 17A cut along a line A-A'. Hereinafter, descriptions overlapping those of the X-ray detector 1000 according to the third embodiment of the present disclosure will be omitted. FIG. 16 shows a case in which the structure for preventing the movement of the middle block shown in FIG. 17A is applied.

As shown in FIGS. 16 to 18, an X-ray detector 2000 may include the main body 310. The main body 310 may form the exterior of the X-ray detector 2000. The main body 310 may be shaped like a box with one side open.

The main body 310 may further include the battery receptacle 1100. The battery receptacle 1100 may be formed in the bottom plate 1010 of the main body 310 so that the battery 395 could be accommodated. Specifically, the battery receptacle 1100 may be formed at the central portion of the bottom plate 1010 of the main body 310. That is, the battery receptacle 1100 may be formed in the bottom plate 1010 of the main body 310 so as to be spaced apart from the edge of the bottom plate 1010 by a predetermined distance inward of the bottom plate 1010. The battery receptacle 1100 may be defined by the bottom plate 1010 of the main body 310 and the middle block 1920.

The main body 310 may further include the battery receptacle frame 1200. The battery receptacle frame 1200 may be formed in the bottom plate 1010 of the main body 310 along the circumference of the battery receptacle 1100. That is, the battery receptacle frame 1200 may be formed in the bottom plate 1010 of the main body 310 along the outer edge of the battery receptacle 1100. The battery receptacle frame 1200 may be recessed from the bottom plate 1010 of the main body 310 to have a predetermined depth. The battery cover 390a may be coupled to the battery receptacle frame 1200.

The main body 310 may further include the partition 1300. The partition 1300 may be formed in the bottom plate 1010 of the main body 310 to partition the battery receptacle 1100 into a plurality of spaces. As an example, the partition 1300 may be formed in the bottom plate 1010 of the main body 310 to partition the battery receptacle 1100 into two spaces. One end of the partition 1300 may be connected to one side of the battery receptacle frame 1200 facing each other and the other end of the partition 1300 may be connected to the other side of the battery receptacle frame 1200 facing each other. The partition 1300 may divide the battery receptacle 1100 into a plurality of spaces having the same size or a plurality of spaces having different sizes. The number and size of the plurality of spaces of the battery receptacle 1100 partitioned by the partition 1300 may correspond to the number and size of the plurality of batteries accommodated in the plurality of spaces.

The main body 310 may further include the plurality of guide holes 1400. The plurality of guide holes 1400 may be formed in the bottom plate 1010 of the main body 310 along the circumference of the battery receptacle 1100. Specifically, the plurality of guide holes 1400 may be formed in the battery receptacle frame 1200 to guide the engagement position of a plurality of fixing members 1800. The plurality of fixing members 1800 may be coupled to the plurality of bosses 1500 formed in the middle block 1920 through the plurality of guide holes 1400. The plurality of guide holes 1400 may be formed to be spaced apart from each other. The plurality of guide holes 1400 may have a hole shape with one side opened. However, a shape of the plurality of guide holes 1400 is not limited to the above-described example, and may be variously changed. As an example, the plurality of guide holes 1400 may have various shapes such as a circular shape, an elliptical shape, and a polygonal shape.

As shown in FIGS. 17A and 18, the main body 310 may further include a plurality of coupling bosses 1950. The plurality of coupling bosses 1950 may be formed in the bottom plate 1010 of the main body 310 to have a hollow. Specifically, the plurality of coupling bosses 1950 may be formed in the partition 1300 so as to have the hollow. The plurality of coupling bosses 1950 may be spaced apart from each other in a longitudinal direction of the partition 1300. The plurality of coupling bosses 1950 may be protruded toward the battery cover 390a to have a constant height. The plurality of coupling bosses 1950 may have a cylindrical shape with a hollow, but a shape of the plurality of coupling bosses 1950 is not limited to the above example.

The middle block 1920 may further include a plurality of coupling projections 1960. The plurality of coupling projections 1960 may be formed in the middle block 1920 to correspond to the plurality of coupling bosses 1950. The plurality of coupling projections 1960 may be formed to protrude from the second surface 1912 of the middle block 1920. The plurality of coupling projections 1960 may be coupled to the plurality of coupling bosses 1950. Specifically, the plurality of coupling projections 1960 may be inserted into the hollows of the plurality of coupling bosses 1950 and coupled to the plurality of coupling bosses 1950.

As shown in FIG. 17B, the main body 310 may further include the plurality of coupling bosses 1950. The plurality of coupling bosses 1950 may be formed in the bottom plate 1010 of the main body 310 to have the hollow. Specifically, the plurality of coupling bosses 1950 may be formed in the battery receptacle frame 1200 to have the hollow. The plurality of coupling bosses 1950 may be formed on both sides of the battery receptacle frame 1200 facing each other. Specifically, the plurality of coupling bosses 1950 may be formed on both sides of the battery receptacle frame 1200 parallel to the partition 1300. In other words, the battery receptacle frame 1200 may include a plurality of long sides facing each other and a plurality of short sides connected to the plurality of long sides to form the battery receptacle frame 1200. The plurality of guide holes 1400 may be formed in each of the plurality of long sides, and the plurality of coupling bosses 1950 may be formed in each of the plurality of short sides. At this time, the plurality of short sides may be parallel to the partition 1300. The plurality of coupling bosses 1950 may be protruded toward the battery cover 390a to have a constant height. The plurality of coupling bosses 1950 may have a cylindrical shape with a hollow, but the shape of the plurality of coupling bosses 1950 is not limited to the above example. The plurality of coupling projections 1960 formed in the middle block 1920 may be coupled to the plurality of coupling bosses 1950.

As shown in FIG. 17C, the main body 310 may further include the plurality of coupling bosses 1950. The plurality of coupling bosses 1950 may be formed in the bottom plate 1010 of the main body 310 to have a hollow. The plurality of coupling bosses 1950 may be protruded toward the battery cover 390a to have a constant height. The plurality of coupling bosses 1950 may have a cylindrical shape with a hollow, but the shape of the plurality of coupling bosses 1950 is not limited to the above example. The plurality of coupling projections 1960 formed in the middle block 1920 may be coupled to the plurality of coupling bosses 1950. A part of the plurality of coupling bosses 1950 may be formed in the partition 1300 as described in FIG. 17A, and another part of the plurality of coupling bosses 1950 may be formed in the battery receptacle frame 1200 as described in FIG. 17B.

When an external force is applied to the X-ray detector 2000, a movement of the middle block 1920 may occur. The plurality of fixing members 1800 may prevent the movement of the middle block 1920 primarily by engaging the middle block 1920 with the main body 310. The plurality of coupling projections 1960 may prevent the movement of the middle block 1920 by coupling the middle block 1920 to the main body 310 through an engagement with the plurality of coupling bosses 1950. By implementing various structures that prevent the movement of the plurality of middle blocks 1920 in the X-ray detector 2000, it is possible to effectively prevent the middle block 1920 from moving when an external force is applied to the X-ray detector 2000. It is also possible to prevent a movement of the detector panel 120 disposed on the middle block 1920 and moving integrally with the middle block 1920. Therefore, damage of the detector panel 120, which could occur when the detector panel 120 collides with the main body 310, may be minimized.

Figure 19:
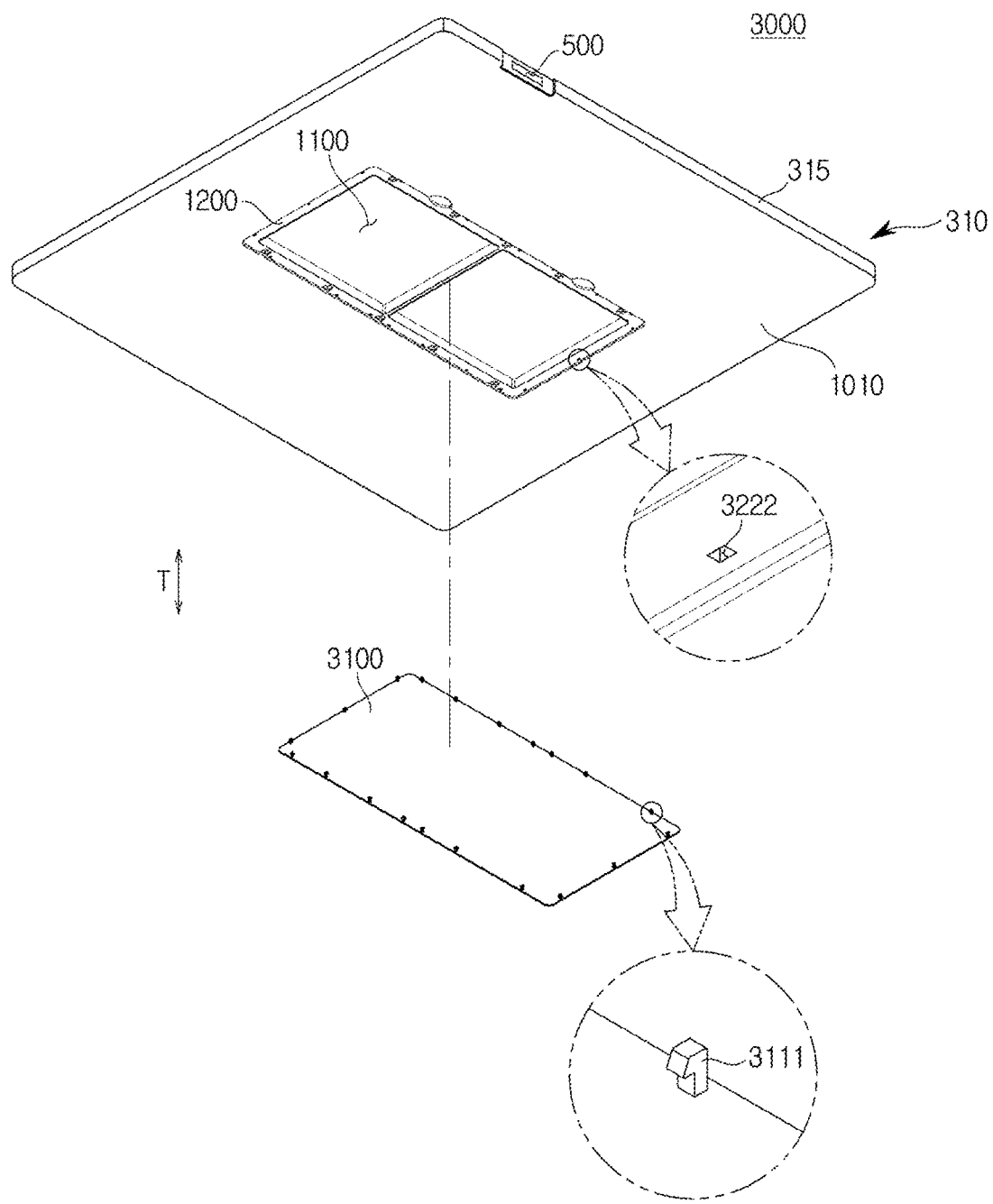
FIG. 19 illustrates a view showing a state in which a battery cover is separated, according to a fifth embodiment of the present disclosure.

FIG. 19 illustrates a view showing a state in which a battery cover is separated, according to a fifth embodiment of the present disclosure. Hereinafter, descriptions overlapping those of the X-ray detector 1000 according to the third embodiment of the present disclosure will be omitted. In FIG. 19, reference numeral "3000" refers to an X-ray detector according to the fifth embodiment of the present disclosure.

As shown in FIG. 19, a battery cover 3100 may include a plurality of protrusions 3111. The plurality of protrusions 3111 may be formed to have a predetermined elasticity. The plurality of protrusions 3111 may be formed along an edge of the battery cover 3100. In other words, the plurality of protrusions 3111 may be formed along an inner circumference of the battery cover 3100. The plurality of protrusions 3111 may protrude from one surface of the battery cover 3100 facing the battery receptacle 1100.

The main body 310 may further include a plurality of protrusion engagement grooves 3222. The plurality of protrusion engagement grooves 3222 may be formed in the bottom plate 1010 of the main body 310 so as to correspond to the plurality of protrusions 3111. Specifically, the plurality of protrusion engagement grooves 3222 may be formed in the battery receptacle frame 1200 of the main body 310. The plurality of protrusions 3111 may be detachably coupled to the plurality of protrusion engagement grooves 3222.

The battery cover 3100 may be formed with a sealing member (not shown) to prevent foreign matter from entering the battery receptacle 1100. The sealing member may be formed on one side of the battery cover 3100 facing the battery receptacle 1100. The sealing member may be an elastic body such as silicone, rubber or the like.

According to embodiments of the present disclosure, a buffer member may be arranged on at least part of a joining groove to prevent a detector panel from being damaged from an external shock applied to the X-ray detector.

Furthermore, a middle block may be fixed on the bottom plate of the main body with a fixing member to prevent a detector panel from being damaged from an external shock applied onto the X-ray detector.

The detector panel may also be protected from appearance deformation of the X-ray detector from an external force by forming the appearance of the X-ray detector using the main body with one side open instead of using extra components, such as a bottom frame and a side frame.

In addition, the external shock applied to the main body may be prevented from being directly delivered to the detector panel by arranging the detector panel inside the main body spaced apart from the main body.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An X-ray imaging apparatus comprising:
   an X-ray source configured to generate and irradiate X-rays; and
   an X-ray detector configured to detect the X-rays irradiated from the X-ray source, the X-ray detector comprising:
      a main body having a bottom plate including a joining groove;
      a detector panel arranged inside the main body, the detector panel is configured to convert X-rays irradiated from the X-ray source into electric signals;
      a middle block arranged inside the main body, the middle block is configured to support the detector panel and includes a boss configured to protrude toward the bottom plate of the main body and be inserted into the joining groove; and
      a buffer member arranged in at least part of the joining groove and configured to prevent the boss from coming into contact with the joining groove,
      wherein the bottom plate includes an uplift part bent to an inside of the X-ray detector, the uplift part is configured to form a battery receptacle on an outer side of the bottom plate and form a wall of the joining groove, and
      wherein the buffer member and the boss are on an opposite side of the bottom plate than the battery receptacle.

2. The X-ray imaging apparatus of claim 1, wherein the buffer member includes a first buffer member arranged along a periphery of the uplift part.

3. The X-ray imaging apparatus of claim 2, wherein the bottom plate further includes a rib extending to the inside of the X-ray detector, the rib is located outside of the uplift part and configured to form another wall of the joining groove, and
   wherein the buffer member further includes a second buffer member arranged along the periphery of the rib.

4. The X-ray imaging apparatus of claim 2, wherein the middle block is supported on the uplift part.

5. The X-ray imaging apparatus of claim 2, wherein the X-ray detector further comprises a battery cover detachably combined onto the bottom plate of the main body.

6. The X-ray imaging apparatus of claim 1, wherein the buffer member has the form of a closed loop.

7. The X-ray imaging apparatus of claim 1, wherein the detector panel is arranged inside the main body to be spaced apart from the main body.

8. The X-ray imaging apparatus of claim 1, wherein the main body further comprises a side wall extending from the bottom plate in a direction corresponding to a width of the X-ray detector, and
   wherein the middle block is arranged inside the main body to be spaced apart from the side wall.

9. An X-ray detector for detecting X-rays, the X-ray detector comprising:
   a main body including a bottom plate having a joining groove and a side wall extending from the bottom plate in a direction corresponding to a width of the X-ray detector;
   a detector panel arranged inside the main body spaced apart from the main body, the detector panel is configured to convert the X-rays into electric signals;
   a middle block arranged inside the main body and configured to support the detector panel, the middle block is spaced apart from a side wall of the main body and includes a boss configured to protrude toward the bottom plate of the main body and be inserted into the joining groove;
   a shock transfer path formed across the side wall and the bottom plate of the main body; and
   a buffer member arranged in the shock transfer path and configured to prevent an external shock from being delivered to the detector panel,
   wherein the bottom plate includes an uplift part bent to an inside of the X-ray detector, the uplift part is configured to form a battery receptacle on an outer side of the bottom plate and form a wall of the joining groove, and
   wherein the buffer member and the boss are on an opposite side of the bottom plate than the battery receptacle.

10. The X-ray detector of claim 9, wherein the buffer member is arranged in the joining groove.

11. The X-ray detector of claim 9, wherein the buffer member has the form of a closed loop.

12. The X-ray detector of claim 9, wherein
    the buffer member is arranged along a girth of the uplift part to face the boss.

13. The X-ray detector of claim 9, wherein the bottom plate comprises a rib extending to the inside of the X-ray detector, the ribs is in parallel with the side wall and spaced apart from the side wall of the main body, the rib is configured to form a wall of the joining groove, and
    wherein the buffer member is disposed adjacent to the rib.

14. The X-ray detector of claim 13, wherein the buffer member is disposed adjacent to the rib to face the boss.

15. An X-ray imaging apparatus comprising:
    an X-ray source configured to generate and irradiate X-rays; and
    an X-ray detector configured to detect the X-rays irradiated from the X-ray source, the X-ray detector comprising:
       a main body having a bottom plate including a joining groove;
       a detector panel arranged inside the main body, the detector panel configured to convert X-rays irradiated from the X-ray source into electric signals;

a middle block arranged inside the main body to support the detector panel, the middle block having a boss formed to protrude toward the bottom plate of the main body and configured to be inserted into the joining groove; and a fixing member combined onto the bottom plate in an opposite direction to a direction in which the boss is configured to be inserted into the joining groove, the fixing member configured to prevent movement of the middle block thereby fixing the middle block onto the bottom plate, wherein the fixing member passes through the bottom plate to be combined with the boss of the middle block.

16. The X-ray imaging apparatus of claim 15, wherein the detector panel is arranged inside the main body to be spaced apart from the main body.

17. The X-ray imaging apparatus of claim 15, wherein the main body further comprises a side wall extending from the bottom plate in a direction corresponding to a width of the X-ray detector, and wherein the middle block is arranged inside the main body to be spaced apart from the side wall.

18. The X-ray imaging apparatus of claim 15, wherein the bottom plate includes an uplift part bent to an interior of the X-ray detector, the uplift part is configured to form a battery receptacle on an outer side of the bottom plate and form a wall of the joining groove, and wherein the boss is inserted into the joining groove to be spaced apart from the uplift part.

19. The X-ray imaging apparatus of claim 18, wherein the bottom plate further includes a rib extending to the inside of the X-ray detector to be located outside of the uplift part and configured to form another wall of the joining groove, and wherein the boss is inserted into the joining groove to be spaced apart from the uplift part.

* * * * *